United States Patent
Chevet et al.

(10) Patent No.: US 11,467,160 B2
(45) Date of Patent: Oct. 11, 2022

(54) METHOD OF THERAPY SELECTION FOR PATIENT SUFFERING FROM GLIOBLASTOMA

(71) Applicants: INSERM (Institut National de la Santé et de la Recherche Médicale), Paris (FR); Université de Rennes 1, Rennes (FR); Centre Eugene Marquis, Rennes (FR); Enios Applications Private Limited Company, Kallithea Athens (GR)

(72) Inventors: Eric Chevet, Rennes (FR); Tony Avril, Rennes (FR); Aristotelis Chatziioannou, Kallithea Athens (GR)

(73) Assignees: INSERM (INSTITUT NAITONAL DE LA SANTÉ ET DE LA RECHERCHE MÉDICALE), Paris (FR); UNIVERSITÉ DE RENNES I, Rennes (FR); CENTRE EUGENE MARQUIS, Rennes (FR); ENIOS APPLICATIONS PRIVATE LIMITED COMPANY, Athens (GR)

( * ) Notice: Subject to any disclaimer, the term of this patent is extended or adjusted under 35 U.S.C. 154(b) by 269 days.

(21) Appl. No.: 16/612,153

(22) PCT Filed: May 9, 2018

(86) PCT No.: PCT/EP2018/062006
§ 371 (c)(1),
(2) Date: Nov. 8, 2019

(87) PCT Pub. No.: WO2018/206644
PCT Pub. Date: Nov. 15, 2018

(65) Prior Publication Data
US 2021/0080461 A1    Mar. 18, 2021

(30) Foreign Application Priority Data
May 11, 2017    (EP) .................................. 17305535

(51) Int. Cl.
*G01N 33/574*    (2006.01)
*A61P 35/00*    (2006.01)
*A61K 31/506*    (2006.01)

(52) U.S. Cl.
CPC ..... *G01N 33/57407* (2013.01); *A61K 31/506* (2013.01); *A61P 35/00* (2018.01); *G01N 33/57492* (2013.01); *G01N 2333/70503* (2013.01)

(58) Field of Classification Search
None
See application file for complete search history.

(56) References Cited

PUBLICATIONS

Zhu et al. "CD90 is upregulated in gastric cancer tissues and inhibits gastric cancer cell apoptosis by modulating the expression level of SPARC protein," Oncology Reports 34: 2497-2506, 2015. (Year: 2015).*
Shi et al. "Synergistic antitumor effects of dasatinib and oxaliplatin in gastric cancer cells," Cancer Chemother Pharmacol (2013) 72: 35-44. (Year: 2013).*
He at al. "CD90 is Identified as a Candidate Marker for Cancer Stem Cells in Primary High-Grade Gliomas Using Tissue Microarrays," Molecular & Cellular Proteomics 11:10.1074/mcp.M111.010744, 1-8, 2012. (Year: 2012).*
Milano et al. "Dasatinib-induced autophagy is enhanced in combination with temozolomide in glioma," Mol Cancer Ther 2009;8(2). Feb. 2009. (Year: 2009).*
Bahnassy et al.; "Aberrant expression of cancer stem cell markers (CD44, CD90, and CD133) contributes to disease progression and reduced survival in hepatoblastoma patients: 4-year survival data"; Translational Research, vol. 165, No. 3, 1 Mar. 20, 2015, pp. 396-406.
Campioni et al.; "A decreased positivity for CD90 on human mesenchymal stromal cells (MSCs) is associated with a loss of immunosuppressive activity by MSCs"; Cytometry. Part B, Clinical Cytometry, vol. 768, No. 3, May 1, 2009, pp. 225-230.
He et al.; "CD90 is Identified as a Candidate Marker for Cancer Stem Cells in Primary High-Grade Gliomas Using Tissue Microarrays"; Molecular and Cellular Proteomics, vol. 11, No. 6, Jun. 1, 2012, the whole document.
Kang et al.; "Tumorigenesis of Chemotherapeutic Drug-Resistant Cancer Stem-Like Cells in Brain Glioma"; Stem Cells and Development, vol. 16, No. 5, Oct. 1, 2007, pp. 837-848.
Kitayama et al.; "CD90(+) Mesothelial-Like Cells in Peritoneal Fluid Promote Peritoneal Metastasis by Forming a Tumor Permissive Microenvironment"; PLOS One, vol. 9, No. 1, Jan. 21, 2014, pp. e86516-1.
Amoui et al.; "SRC Family Selective Tyrosine Kinase Inhibitor, PP1, Inhibits Both FCepsilonRI- and Thy-1-Mediated Activation of Rat Basophilic Leukemia Cells"; European Journal of Immunology, vol. 27, No. 8, Aug. 1, 1997, pp. 1881-1886.
Milano et al.; "Dasatinib-induced autophagy is enhanced in combination with temozolomide in glioma"; Molecular Cancer Therapeutics, vol. 8, No. 2, Jan. 27, 2009, pp. 394-406.

* cited by examiner

*Primary Examiner* — Jeffrey S Lundgren
*Assistant Examiner* — Michael J Schmitt
(74) *Attorney, Agent, or Firm* — WCF IP

(57) ABSTRACT

The present invention relates to method of therapy selection for patient suffering from glioblastoma. Using in vitro and in vivo approaches, the inventors demonstrated the critical role of CD90 in GBM migration/invasion. They showed that CD90 signaling though SRC, FAK and RhoA promotes cell migration and importantly, that high CD90 expression impacts on the cell response to the SRC inhibitor dasatinib. In particular, the present invention relates to a method for predicting whether a subject will be eligible to a treatment with a drug selected from the group consisting of SRC inhibitor, FAK inhibitor or RhoA inhibitor by determining the expression level of CD90 in a sample obtained from the subject.

5 Claims, 14 Drawing Sheets

F

Figure 1A:
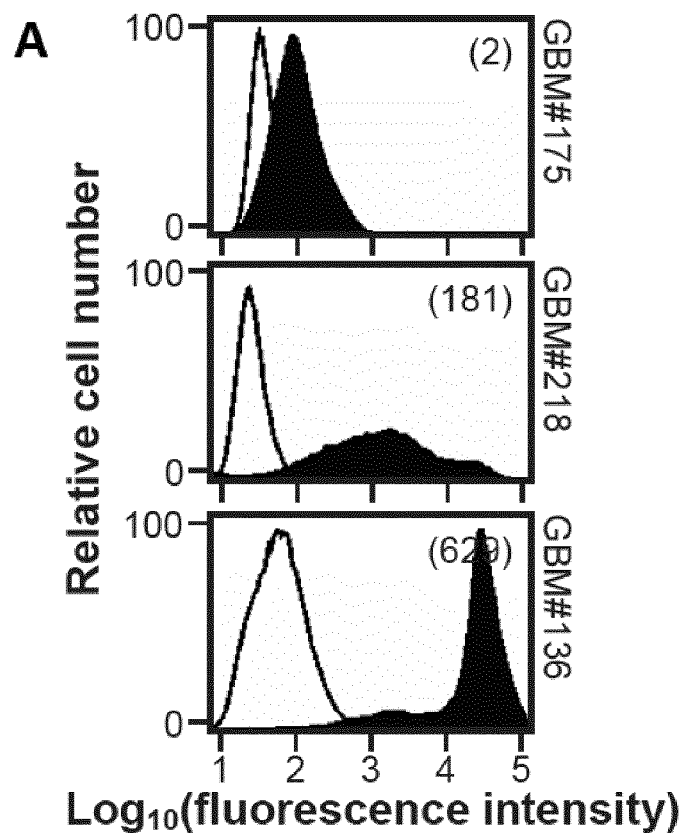

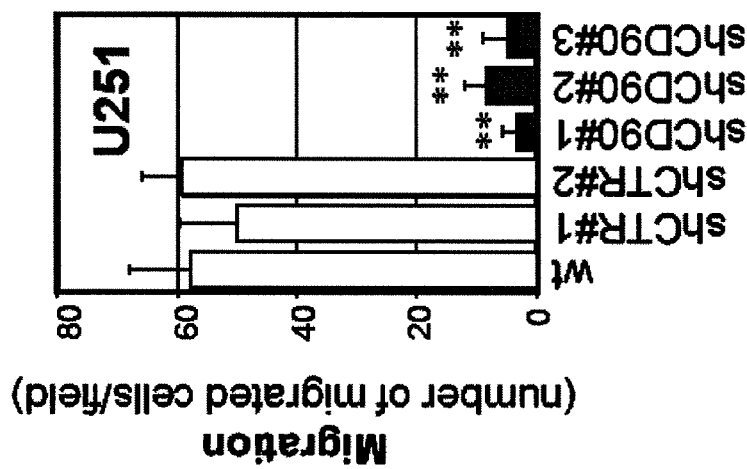
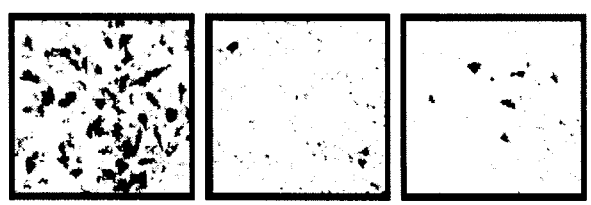
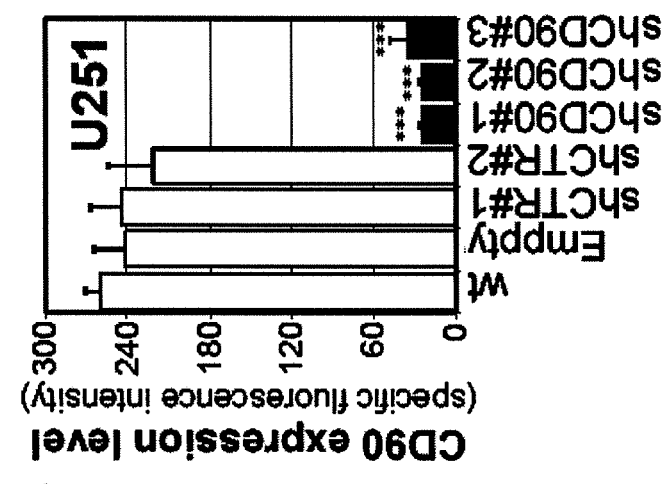
FIGURES 2A & 2B

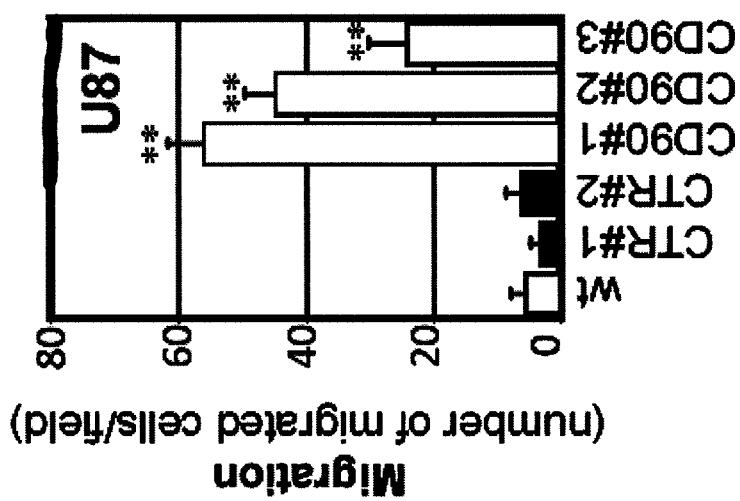
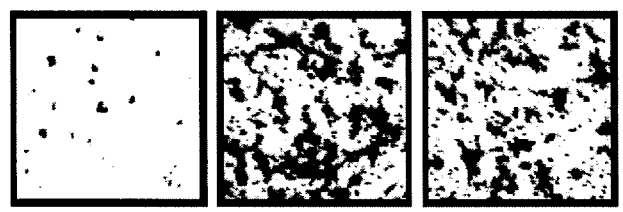
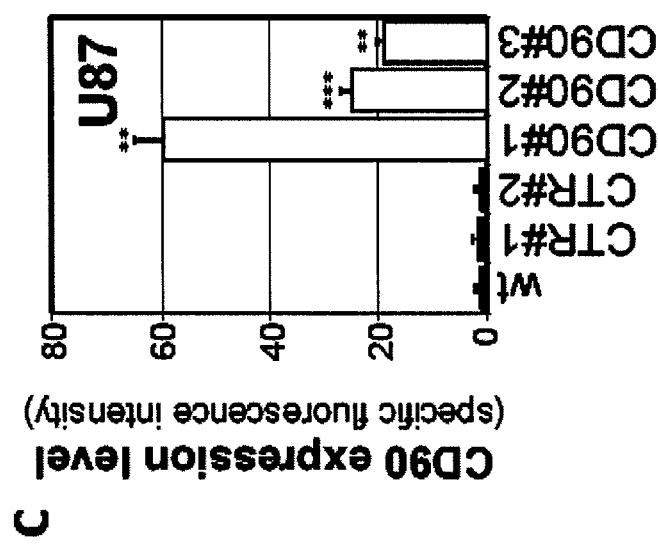
FIGURES 2C & 2D

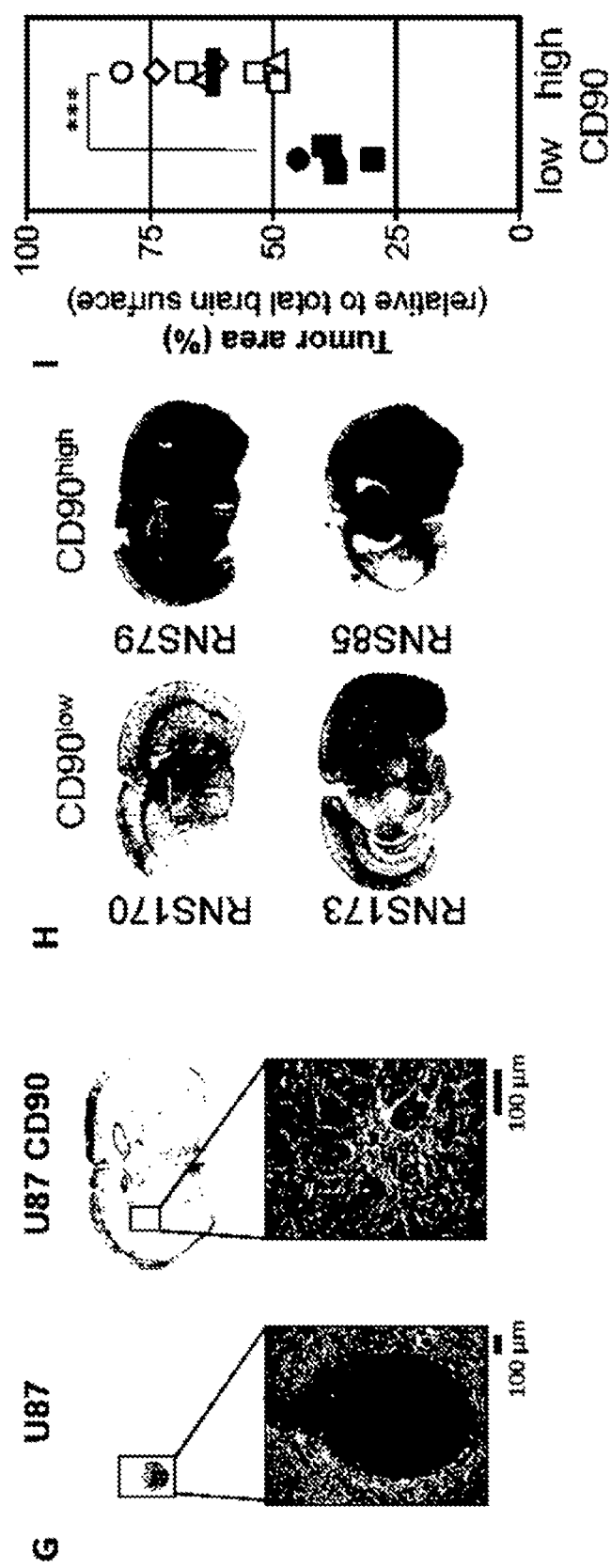
FIGURES 2G, 2H, & 2I

METHOD OF THERAPY SELECTION FOR PATIENT SUFFERING FROM GLIOBLASTOMA

FIELD OF THE INVENTION

The present invention relates to method of therapy selection for patient suffering from glioblastoma.

BACKGROUND OF THE INVENTION

Glioblastoma (GBM) is one of the deadliest human cancers with an incidence of about 3.5/100,000 per year worldwide (Cloughesy, T. F., W. K. Cavenee, and P. S. Mischel, Glioblastoma: from molecular pathology to targeted treatment. Annu Rev Pathol, 2014. 9: p. 1-25). Despite the aggressive standard of care currently used including surgery, chemo- and radiotherapy, the prognosis remains very poor with ~15 months overall survival (Weathers, S. P. and M. R. Gilbert, Advances in treating glioblastoma. F1000Prime Rep, 2014. 6: p. 46). The inevitable recurrence of GBM is associated to: (i) resistance to radio and chemo-therapy; (ii) diffuse features due to the invasiveness properties of tumor cells throughout the surrounding brain parenchyma and (iii) heterogeneity observed between GBM patients but also within the same tumor (Cloughesy, T. F., W. K. Cavenee, and P. S. Mischel, Glioblastoma: from molecular pathology to targeted treatment. Annu Rev Pathol, 2014. 9: p. 1-25) (Huse, J. T., E. Holland, and L. M. DeAngelis, Glioblastoma: molecular analysis and clinical implications. Annu Rev Med, 2013. 64: p. 59-70).

CD90 (Thy-1) is a marker for mesenchymal stromal/stem cells (Bradley, J. E., G. Ramirez, and J. S. Hagood, Roles and regulation of Thy-1, a contextdependent modulator of cell phenotype. Biofactors, 2009. 35(3): p. 258-65) and has recently been reported on human GBM stem cells (GSCs) (He, J., et al., CD90 is identified as a candidate marker for cancer stem cells in primary high-grade gliomas using tissue microarrays. Mol Cell Proteomics, 2012. 11(6): p. M111 010744.), GBM-associated stromal cells (GASCs) (Clavreul, A., et al., Isolation of a new cell population in the glioblastoma microenvironment. J Neurooncol, 2012. 106 (3): p. 493-504) and mesenchymal stem cell-like pericytes (Ochs, K., et al., Immature mesenchymal stem cell-like pericytes as mediators of immunosuppression in human malignant glioma. J Neuroimmunol, 2013. 265(1-2): p. 106-16.), thereby reflecting the cellular heterogeneity in GBM. CD90 is a N-glycosylated, glycophosphatidylinositol (GPI)—anchored cell surface protein, originally described on murine thymocytes (Haeryfar, S. M. and D. W. Hoskin, Thy-1: more than a mouse pan-T cell marker. J Immunol, 2004. 173(6): p. 3581-8.). CD90 is also expressed on many cell types including endothelial cells, fibroblasts and neurons (Bradley, J. E., G. Ramirez, and J. S. Hagood, Roles and regulation of Thy-1, a context dependent modulator of cell phenotype. Biofactors, 2009. 35(3): p. 258-65) (Rege, T. A. and J. S. Hagood, Thy-1 as a regulator of cell-cell and cell-matrix interactions in axon regeneration, apoptosis, adhesion, migration, cancer, and fibrosis. FASEB J, 2006. 20(8): p. 1045-54) (Barker, T. H. and J. S. Hagood, Getting a grip on Thy-1 signaling. Biochim Biophys Acta, 2009. 1793(5): p. 921-3) (Leyton, L. and J. S. Hagood, Thy-1 modulates neurological cell-cell and cell-matrix interactions through multiple molecular interactions. Adv Neurobiol, 2014. 8: p. 3-20). CD90 has been involved in neurite outgrowth inhibition, T-cell activation and apoptosis, leukocytes and melanoma cell adhesion and migration, tumor suppression in ovarian cancers and fibroblast proliferation and migration in wound healing and fibrosis. Although the exact CD90 mechanisms of action remain unclear, a role in cell-cell/matrix interactions has been proposed (Rege, T. A. and J. S. Hagood, Thy-1 as a regulator of cell-cell and cell-matrix interactions in axon regeneration, apoptosis, adhesion, migration, cancer, and fibrosis. FASEB J, 2006. 20(8): p. 1045-54) (Leyton, L. and J. S. Hagood, Thy-1 modulates neurological cell-cell and cell-matrix interactions through multiple molecular interactions. Adv Neurobiol, 2014. 8: p. 3-20). However, to date, the state of the art does not describe the involvement of CD90 in GBM mechanism (Seon Rang Woo et al., Glioblastoma specific antigens, GD2 and CD90, are not involved in cancer stemness. Anat Cell Biol. 2015 March; 48(1):44-53).

SUMMARY OF THE INVENTION

The present invention relates to method of therapy selection for patient suffering from glioblastoma. In particular, the present invention is defined by the claims.

DETAILED DESCRIPTION OF THE INVENTION

Interestingly, the inventors showed that CD90 expression is not only restricted to GBM stem-like cells but is also observed on differentiated GBM cells (primary adherent lines) and on freshly dissociated GBM specimens. In GBM patients, CD90 is also associated with a cell adhesion/migration gene signature and with multifocal/multicentric and enhancing tumor crossing midline MRI features. Using in vitro and in vivo approaches, the inventors demonstrated the critical role of CD90 in GBM migration/invasion. They showed that CD90 signaling though SRC, FAK and RhoA promotes cell migration and importantly, that high CD90 expression impacts on the cell response to the SRC inhibitor dasatinib. The inventors propose a model in which CD90 expression might represent a novel stratification tool to select patients to be treated with dasatinib. Moreover, their data show that dasatinib would impair not only the adhesion/migration of CD90 high differentiated tumor cells but also the proliferation of $CD90^{high}$ GSCs, thereby increasing its therapeutic potential.

Prediction Methods of the Invention

A first aspect of the present invention relates to a method for predicting whether a subject will be eligible to a treatment with a drug selected from the group consisting of SRC inhibitor, FAK inhibitor or RhoA inhibitor comprising i) determining the expression level of CD90 in a sample obtained from the subject, ii) comparing the expression level determined a step i) with a predetermined reference level and iii) and concluding that the subject will be eligible to a treatment with a drug selected from the group consisting of SRC inhibitor, FAK inhibitor or RhoA inhibitor when the level determined at step i) is higher than the predetermined reference level or concluding that the subject will not be eligible to a treatment with a drug selected from the group consisting of SRC inhibitor, FAK inhibitor or RhoA inhibitor when the level determined at step i) is lower that the predetermined expression level.

Another aspect of the present invention relates to a method of treating glioblastoma in a subject in need thereof comprising i) predicting whether a subject will be eligible to a treatment with a drug selected from the group consisting of SRC inhibitor, FAK inhibitor or RhoA inhibitor by performing the method of the invention and ii) administering to the subject a therapeutically effective amount of a drug selected from the group consisting of SRC inhibitor, FAK inhibitor or RhoA inhibitor when it is concluded that the subject will be eligible to a treatment with a drug selected from the group consisting of SRC inhibitor, FAK inhibitor or RhoA inhibitor.

As used herein, the term glioblastoma (GBM), also called glioblastoma multiforme or "grade IV astrocytoma" according to WHO classification, has its general meaning in the art and refers to central nervous system primary tumor derived from glial cells. GBM is one of the deadliest human cancers with an incidence of about 3.5/100,000 per year worldwide (Cloughesy, T. F., W. K. Cavenee, and P. S. Mischel, Glioblastoma: from molecular pathology to targeted treatment. Annu Rev Pathol, 2014. 9: p. 1-25). Despite the aggressive standard of care currently used including surgery, chemo- and radiotherapy, the prognosis remains very poor with ~15 months overall survival (Weathers, S. P. and M. R. Gilbert, Advances in treating glioblastoma. F1000Prime Rep, 2014. 6: p. 46).

As used herein, the term "subject" denotes a mammal, such as a rodent, a feline, a canine, and a primate. Preferably, a subject according to the invention is a human. In one embodiment, the subject is a non-operable and non-irradiable subject. In one embodiment, the subject has a tumor comprising two or more lobes.

As used herein, the term "sample" refers to any substance of biological origin. Examples of samples includes, but are not limited to blood, tumor, saliva, urine, cerebrospinal fluids, or any of other biological fluids or tissues.

In a preferred embodiment, the sample is tumor sample. As used herein, the term "tumor sample" means any tissue tumor sample derived from the subject. Said tissue sample is obtained for the purpose of the in vitro evaluation. In some embodiments, the tumor sample may result from the tumor resected from the subject. In some embodiments, the tumor sample may result from a biopsy performed in the primary tumor of the subject or performed in metastatic sample distant from the primary tumor of the subject. In some embodiments, the tumor sample is a sample of circulating tumor cells. As used herein, the term "circulating tumor cell" or "CTC" refers to a cancer cell derived from a cancerous tumor that has detached from the tumor and is circulating in the blood stream of the subject. Typically the CTCs are isolated from the blood sample using a filter and/or a marker based method.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. The term "treatment" encompasses the prophylactic treatment. As used herein, the term "prevent" refers to the reduction in the risk of acquiring or developing a given condition.

As used herein, "therapeutically effective amount" means a sufficient amount of SRC inhibitor, FAK inhibitor or RhoA inhibitor for use in a method for the treatment of GBM at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the severity of GBM, the age, body weight, general health, sex and diet of the subject; the time of administration, route of administration, and rate of excretion of the specific compound employed; the duration of the treatment; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The terms "administer" or "administration" refer to the act of injecting or otherwise physically delivering a substance as it exists outside the body (e.g., SRC inhibitor, FAK inhibitor or RhoA inhibitor) into the subject. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

As used herein, the term "predicting" refers to a probability or likelihood for a patient to respond to the treatment with a drug selected from the group consisting of SRC inhibitor, FAK inhibitor or RhoA inhibitor. As used herein, the term "responsiveness" refers to ability to assess the likelihood that treatment will or will not be clinically effective.

As used herein, the term "predetermined reference level" refers to the expression levels of CD90 in samples obtained from the general population or from a selected population of subjects (tumor specimens from GBM patients). A "predetermined reference level" may be determined, for example, by determining the expression level of CD90 nucleic acids or encoded polypeptides, in a corresponding sample obtained from one or more control subject(s). When such a predetermined reference level is used, a higher or increased levels determined in a sample (i.e. a test sample obtained from the subject) is indicative for example that said patient is eligible to a treatment with a drug selected from the group consisting of SRC inhibitor, FAK inhibitor or RhoA inhibitor.

As used herein, the term "CD90" (Cluster of Differentiation 90), also known as Thy-1 (THYmocyte differentiation antigen 1) has its general meaning in the art and refers to a N-glycosylated, glycophosphatidylinositol (GPI)—anchored cell surface protein (Uniprot reference: P04216 for *Homo sapiens* and P01831 for *Mus musculus*). CD90 is encoded by CD90 gene (also called Thy1 gene) (NCBI gene ID: 7070 for *Homo sapiens* and 21838 for *Mus musculus*).

As used herein, the term "SRC" has its general meaning in the art and refers to proto-oncogene tyrosine-protein kinase, also known as proto-oncogene c-Src (Uniprot reference for *Homo sapiens*: P12931). SRC is a non-receptor tyrosine kinase protein that phosphorylates specific tyrosine residues in other proteins. SRC is encoded by SRC gene (NCBI gene ID: 6714 for *Homo sapiens*).

As used herein, the term "FAK" (focal adhesion kinase), also known as PTK2 (protein tyrosine kinase 2), has its general meaning in the art and refers to a focal adhesion-associated protein kinase involved in cellular adhesion and spreading processes (Uniprot reference: Q05397 for *Homo sapiens* and P34152 for *Mus musculus*). FAK is encoded by FAK gene (also called PTK2 gene) (NCBI gene ID: 5747 for *Homo sapiens* and 14083 for *Mus musculus*).

As used herein, the term "RhoA" (Ras homolog gene family, member A) has its general meaning in the art and refers to a small GTPase protein of Rho family (Uniprot reference: P61586 for *Homo sapiens* and Q9QUI0 for *Mus musculus*). RhoA is encoded by RHOA gene (NCBI gene ID: 387 for *Homo sapiens* and 11848 for *Mus musculus*).

As used herein, the term "SRC inhibitor" has its general meaning in the art and refers to any compound, natural or synthetic, that blocks, suppresses, or reduces the biological activity of SRC or to any compound that inhibits SRC gene expression.

As used herein, the term "FAK inhibitor" has its general meaning in the art and refers to any compound, natural or synthetic, that blocks, suppresses, or reduces the biological activity of FAK or to any compound that inhibits FAK gene expression.

As used herein, the term "RhoA inhibitor" has its general meaning in the art and refers to any compound, natural or synthetic, that blocks, suppresses, or reduces the biological activity of RhoA or to any compound that inhibits RHOA gene expression.

In one embodiment, the SRC inhibitor is dasatinib. As used herein, the term "dasatinib" has its general meaning in the art and refers to a cancer drug that inhibits Bcr-Abl tyrosine kinase and Src family tyrosine kinase. The IUPAC name of dasatinib is N-(2-chloro-6-methylphenyl)-2-[[6-[4-(2-hydroxyethyl)piperazin-1-yl]-2-methylpyrimidin-4-yl]amino]-1,3-thiazole-5-carboxamide. The formula (I) of dasatinib is:

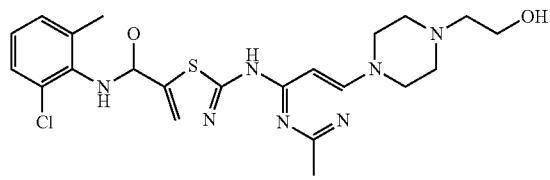

(I)

In one embodiment, the SRC inhibitor is bosutinib. As used herein, the term "bosutinib" has its general meaning in the art and refers to protein kinase inhibitor, and P-glycoprotein inhibitor. The IUPAC name of bosutinib is 4-(2,4-dichloro-5-methoxyanilino)-6-methoxy-7-[3-(4-methylpiperazin-1-yl)propoxy]quinoline-3-carbonitrile. The formula (II) of bosutinib is:

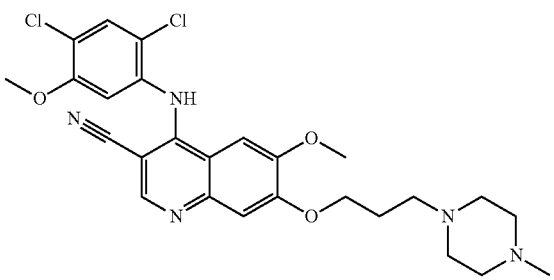

(II)

In one embodiment, the SRC inhibitor is saracatinib. As used herein, the term "saracatinib" has its general meaning in the art and refers to a dual-specific inhibitor of protein tyrosine kinase Src and Abl. The IUPAC name of saracatinib is N-(5-chloro-1,3-benzodioxol-4-yl)-7-[2-(4-methylpiperazin-1-yl)ethoxy]-5-(oxan-4-yloxy)quinazolin-4-amine. The formula (III) of saracatinib is:

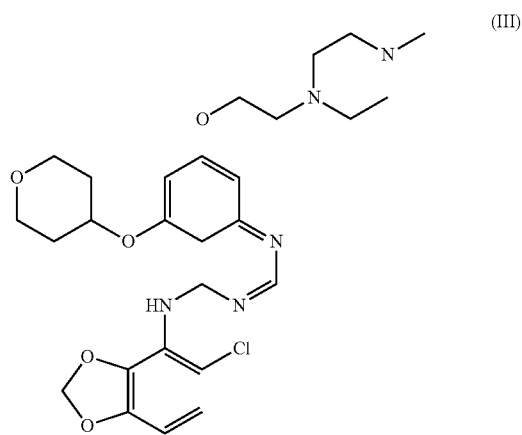

(III)

In one embodiment, the SRC inhibitor is KX2-391. As used herein, the term "KX2-391" has its general meaning in the art and refers to an oral src inhibitor. The IUPAC name of KX2-391 is N-benzyl-2-[5-[4-(2-morpholin-4-ylethoxy)phenyl]pyridin-2-yl]acetamide.

In one embodiment, the RhoA inhibitor is CCG-1423. As used herein, the term "CCG-1423" has its general meaning in the art and refers to a specific inhibitor of Rho pathway-mediated signaling. The IUPAC name of CCG-1423 is N-[1-(4-chloroanilino)-1-oxopropan-2-yl]oxy-3,5-bis(trifluoromethyl)benzamide.

Another examples of SRC inhibitor, FAK inhibitor or RhoA inhibitor are described in the following documents:

Stephen Hiscox PhD & Robert I Nicholson PhD (2008) Src inhibitors in breast cancer therapy, Expert Opinion on Therapeutic Targets, 12:6, 757-767;

Jade Homsi, Christopher Cubitt & Adil Daud (2007) The Src signaling pathway: a potential target in melanoma and other malignancies, Expert Opinion on Therapeutic Targets, 11:1, 91-100;

Alexander Schultze & Walter Fiedler (2010) Therapeutic potential and limitations of new FAK inhibitors in the treatment of cancer, Expert Opinion on Investigational Drugs, 19:6, 777-788;

Bingyu Guo, Jingyuan Su, Tingting Zhang, Kaiwen Wang & Xiaoming Li (2015) Fangchinoline as a kinase inhibitor targets FAK and suppresses FAK-mediated signalling pathway in A549, Journal of Drug Targeting, 23:3, 266-274;

Jianliang Zhang, Di-Hua He, Maria Zajac-Kaye & Steven N Hochwald (2014) A small molecule FAK kinase inhibitor, GSK2256098, inhibits growth and survival of pancreatic ductal adenocarcinoma cells, Cell Cycle, 13:19, 3143-3149;

Isabelle Tanjoni, Colin Walsh, Sean Uryu, Alok Tomar, Ju-Ock Nam, Ainhoa Mielgo, Ssang-Taek Lim, Congxin Liang, Marcel Koenig, Neela Patel, Cheni Kwok, Gerald McMahon, Dwayne G. Stupack & David D. Schlaepfer (2010) PND-1186 FAK inhibitor selectively promotes tumor cell apoptosis in three-dimensional environments, Cancer Biology & Therapy, 9:10, 764-777;

Steven N. Hochwald, Carl Nyberg, Min Zheng, Donghang Zheng, Cheng Wood, Nicole A. Massoll, Andrew Magis, David Ostrov, William G. Cance & Vita M. Golubovskaya (2009) A novel small molecule inhibitor of FAK decreases growth of human pancreatic cancer, Cell Cycle, 8:15, 2435-2443;

Shanthi E et al., Focal adhesion kinase inhibitors in the treatment of metastatic cancer: a patent review. Expert Opin Ther Pat. 2014 October; 24(10):1077-100;

Sabina Antonela Antoniu MD PhD (2012) Targeting RhoA/ROCK pathway in pulmonary arterial hypertension, Expert Opinion on Therapeutic Targets, 16:4, 355-363.

Methods for Determining the Expression Level of CD90:

Determination of the expression level of CD90 gene may be performed by a variety of techniques. Generally, the expression level as determined is a relative expression level. For example, the determination comprises contacting the sample with selective reagents such as probes or ligands, and thereby detecting the presence, or measuring the amount, of nucleic acids or polypeptides of interest originally in said sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the biological sample.

In a particular embodiment of the invention, the expression level of CD90 gene may be determined by determining the quantity of mRNA.

Methods for determining the quantity of mRNA are well known in the art. For example the nucleic acid contained in the samples is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Quantitative or semi-quantitative RT-PCR is preferred. Real-time quantitative or semi-quantitative RT-PCR is particularly advantageous.

Nucleic acids having at least 10 nucleotides and exhibiting sequence complementarity or homology to the mRNA of interest herein find utility as hybridization probes. It is understood that such nucleic acids need not be identical, but are typically at least about 80% identical to the homologous region of comparable size, more preferably 85% identical and even more preferably 90-95% identical. Probes typically comprise single-stranded nucleic acids of between 10 to 1000 nucleotides in length, for instance of between 10 and 800, more preferably of between 15 and 700, typically of between 20 and 500. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

In the context of the invention, "hybridization" relates to the fact of obtaining a close interaction of the nucleotide probe and the target region that is expected to be revealed by the detection of the nucleotide probe. Such an interaction can be achieved by the formation of hydrogen bonds between the nucleotide probe and the target sequence, which is typical of the interactions between complementary nucleotide molecules capable of base pairing. Hydrogen bonds can be found, for example, in the annealing of two complementary strands of DNA.

It will be advantageous to use nucleic acids in combination with appropriate means, such as a detectable label, for detecting hybridization. A wide variety of appropriate indicators are known in the art including, fluorescent, radioactive, enzymatic or other ligands.

Conventional methods and reagents for isolating RNA from a sample comprise High Pure miRNA Isolation Kit (Roche), Trizol (Invitrogen), Guanidinium thiocyanate-phenol-chloroform extraction, PureLink™ miRNA isolation kit (Invitrogen), PureLink Micro-to-Midi Total RNA Purification System (invitrogen), RNeasy kit (Qiagen), Oligotex kit (Qiagen), phenol extraction, phenol-chloroform extraction, TCA/acetone precipitation, ethanol precipitation, Column purification, Silica gel membrane purification, PureYield™ RNA Midiprep (Promega), PolyATtract System 1000 (Promega), Maxwell® 16 System (Promega), SV Total RNA Isolation (Promega), geneMAG-RNA/DNA kit (Chemicell), TRI Reagent® (Ambion), RNAqueous Kit (Ambion), ToTALLY RNA™ Kit (Ambion), Poly(A)Purist™ Kit (Ambion) and any other methods, commercially available or not, known to the skilled person.

In one embodiment, the expression level of one or more mRNAs is determined by the quantitative polymerase chain reaction (QPCR) technique. The QPCR may be performed using chemicals and/or machines from a commercially available platform. The QPCR may be performed using QPCR machines from any commercially available platform; such as Prism, geneAmp or StepOne Real Time PCR systems (Applied Biosystems), LightCycler (Roche), RapidCycler (Idaho Technology), MasterCycler (Eppendorf), BioMark™ HD System (Fluidigm), iCycler iQ system, Chromo 4 system, CFX, MiniOpticon and Opticon systems (Bio-Rad), SmartCycler system (Cepheid), RotorGene system (Corbett Lifescience), MX3000 and MX3005 systems (Stratagene), DNA Engine Opticon system (Qiagen), Quantica qPCR systems (Techne), InSyte and Syncrom cycler system (BioGene), DT-322 (DNA Technology), Exicycler Notebook Thermal cycler, TL998 System (lanlong), LineGene-K systems (Bioer Technology), or any other commercially available platform. The QPCR may be performed using chemicals from any commercially available platform, such as NCode EXPRESS qPCR or EXPRESS qPCR (Invitrogen), Taqman or SYBR green qPCR systems (Applied Biosystems), Real-Time PCR reagents (Eurogentec), iTaq mix (Bio-Rad), qPCR mixes and kits (Biosense), and any other chemicals, commercially available or not, known to the skilled person. The QPCR reagents and detection system may be probe-based, or may be based on chelating a fluorescent chemical into double-stranded oligonucleotides.

The QPCR reaction may be performed in a tube; such as a single tube, a tube strip or a plate, or it may be performed in a microfluidic card in which the relevant probes and/or primers are already integrated.

In a particular embodiment, the expression level of CD90 gene may be determined by determining of the quantity of protein encoded by the CD90 gene.

Such methods comprise contacting the sample with a binding partner capable of selectively interacting with the protein present in said sample. The binding partner is generally an antibody that may be polyclonal or monoclonal, preferably monoclonal.

As used herein, the term "monoclonal antibody" refers to a population of antibody molecules that contains only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the invention.

Laboratory methods for preparing monoclonal antibodies are well known in the art (see, for example, Harlow et al., 1988). Monoclonal antibodies (mAbs) may be prepared by immunizing purified CD90 into a mammal, e.g. a mouse, rat and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; European Patent Publications No. 0239400 to Winter et al. and No. 0125023 to Cabilly et al.

Antibody generation techniques not involving immunisation are also contemplated such as for example using phage display technology to examine naive libraries (from non-immunised animals); see Barbas et al. (1992), and Waterhouse et al. (1993).

Alternatively, binding agents other than antibodies may be used for the purpose of the invention. These may be for instance aptamers, which are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal. As used herein, the term "labelled", with regard to the antibody or aptamer, is intended to encompass direct labeling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art.

The aforementioned assays generally involve the coating of the binding partner (ie. antibody or aptamer) in a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

In another embodiment of the invention, the measurement of CD90 in the sample may be achieved by a cytometric bead array system wherein the antibodies that bind to the biomarkers are coated directly or indirectly on beads. Typically, Luminex® technology which is a new technology based on fluorescent detection using a flow cytometer, microbeads dyed with multiple fluorescent colours and lasers detection may be used. Thus, Luminex® Performance Assay Human CD90 Kit commercialized by R&D Systems, Inc may be used within the context of the invention.

For example, the level of a biomarker protein such as CD90 may be measured by using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; Immunoelectrophoresis; immunoprecipitation.

More particularly, an ELISA method can be used, wherein the wells of a microtiter plate are coated with a set of antibodies against CD90. A sample containing or suspected of containing CD90 is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

Measuring the level of a biomarker protein such as CD90 (with or without immunoassay-based methods) may also include separation of the proteins: centrifugation based on the protein's molecular weight; electrophoresis based on mass and charge; HPLC based on hydrophobicity; size exclusion chromatography based on size; and solid-phase affinity based on the protein's affinity for the particular solid-phase that is use. Once separated, CD90 may be identified based on the known "separation profile" e. g., retention time, for that protein and measured using standard techniques.

Alternatively, the separated proteins may be detected and measured by, for example, a mass spectrometer.

Kits of the Invention

A further object of the invention is a kit suitable for predicting whether a subject will be eligible to a treatment with a drug selected from the group consisting of SRC inhibitor, FAK inhibitor or RhoA inhibitor, comprising:
At least a means for determining the expression level of CD90 in a sample obtained from a subject,
Instructions for use.

Typically the kit may include primers, probes, an antibody, or a set of antibodies. In a particular embodiment, the antibody or set of antibodies are labelled. The kit may also contain other suitably packaged reagents and materials needed for the particular detection protocol, including solid-phase matrices, if applicable, and standards.

The invention will be further illustrated by the following figures and examples. However, these examples and figures should not be interpreted in any way as limiting the scope of the present invention.

FIGURES

FIG. 1: CD90 is expressed by all GBM cells, is associated with adhesion and migration gene signatures and MRI invasive features from GBM patients. Human GBM specimens were dissociated, stained with isotype controls or specific anti-CD90 antibodies and directly analyzed for CD90 protein expression by flow cytometry. Representative histograms are shown in (A). CD90 protein expression levels are expressed as the mean of specific fluorescence intensity of the protein expression determined in at least three different experiments as described in Materials and methods section (B). Three corresponding tumor sections were analyzed by immunohistochemistry for CD90 protein expression (C). Total mRNA from GBM specimens (n=77) was extracted and used for a gene expression profile by transcriptome microarray. GBM patients were divided into two distinct groups CD90low (n=16, blank) and CD90high (n=16, black) tumors according to their CD90 mRNA expression level (D). Specific proteins associated to CD90high group were analyzed for their known interaction by the STRING (confidence score >0.8). A robust network was linked to cell adhesion (blank and black) and cell migration (grey and black) functions (E). MRI of 89 GBM patients from the TCGA dataset were analyzed according to VASARI features. Representative cases are shown in (F): tumors with (i) and without (ii) crossing midline; multicentric tumors (iii, with two discrete foci) and focal tumors (iv). CD90 mRNA expression levels were compared between different VASARI features and were statistically different in GBM patients with focal tumor versus multifocal/multicentric tumors and also in tumors with and without crossing midline (G). (*): $p<0.05$; (**): $p<0.01$.

FIG. 2: CD90 controls GBM cell migration in vitro and in vivo. GBM CD90 positive U251 and CD90 negative U87 cell lines were modified respectively to down- and overexpress CD90 molecule. CD90 expression on parental (wt), control (empty and shCTR #, n=2), CD90-down expressing (shCD90 #, n=3) U251 cells; as well as parental (wt), control (CTR #, n=2) and CD90 expressing (CD90 #, n=3) U87 cells was analyzed by flow cytometry as described in FIG. 1 (A and C). Parental (wt), control (empty and shCTR #, n=2), CD90-down expressing (shCD90 #, n=3) U251 cells (B); parental (wt), control (CTR #, n=2) and CD90 expressing (CD90 #, n=3) U87 cells (D); as well as CD90low (blue) and CD90high (orange) RNS (n=4, square symbol) and RADH (n=4, circle symbol) (E) cells were tested in a 24-hours Boyden chamber migration assay as described in Materials and methods section. Representative fields are shown in (B, D, E). The migration index corresponded to the number of migrating cells obtained per field. Control sh #CTR and CD90-down expressing sh #CD90 RNS (n=3, square symbol) and RADH (n=3, circle symbol) cells were tested in a 24-hours Boyden chamber migration assay and representative fields are shown in (F). Parental and CD90-expressing U87 cells (G) or CD90low and CD90high RNS cells (H and I) were orthotopically implanted in immunocompromised mice brain. Mice bearing parental (n=7) and U87 CD90 (n=7) cells were sacrificed 28 days after injection; for RNS cells, mice were sacrificed when the clinical signs appeared. Brains were collected and sections were analyzed after H&E staining (G) or for vimentin expression by immunohistochemistry (H). Posterior section sides are shown in (G) for U87 cells and (H) for RNS cells. Tumor area was determined as described in Materials and methods section (I). (): $p<0.01$; (*): $p<0.001$.

FIG. 3: CD90 signals through SRC, FAK and RhoA molecules and CD90 dependent migration is blocked by dasatinib in vitro and in vivo. Parental (wt), control (shCTR #), CD90-down expressing (shCD90 #, n=3) U251 cells; as well as parental (wt), control (CTR #) and CD90 expressing (CD90 #, n=3) U87 cells were cultured at low cell density, lysed and analyzed by Western-blot for phosphoSRC, SRC, phosphoFAK, FAK and β-actin expression. Protein phosphorylation levels were calculated as described in Materials and Methods part (A). CD90low (black) and CD90high (blank) RNS (n=12, square symbol) and RADH (n=6, circle symbol) cells were analyzed by Western-blot for phosphoSRC, SRC, phosphoFAK, FAK and β-actin expression. Protein phosphorylation levels were calculated in (B). CD90-expressing parental U251 and CD90 #1 U87 cells were tested in a 24-hours Boyden chamber migration assay as described in FIG. 2 in the presence of DMSO (as control), PP2, dasatinib (both SRC inhibitors), Y15 (FAK inhibitor) and Y-27632 (ROCK inhibitor) (C). CD90-expressing parental U251 and CD90 #1 U87 cells were transfected without (siØ), with siRNA GL2 (control) or siRNA RhoA during 48 hours, and tested in a 24-hours Boyden chamber migration assay (D). RhoA expression was tested by Western-blot (D). Migration was given by the number of migrated cells obtained per field (C and D). CD90high RNS (n=4, square symbol) and RADH (n=4, circle symbol) cells were tested in a 24-hours Boyden chamber migration assay in the presence of DMSO or dasatinib (E). Representative fields are shown in (E). CD90 expressing U87 cells were orthotopically implanted in immunocompromised mice brain. One week after injection, mice were fed with control vehicle (n=7) or dasatinib (40 mg/kg/day, n=7) for 20 days. Control and dasatinib-treated mice were sacrificed 28 days after injection. Brains were collected and sections were analyzed after H&E staining (F). (*): p<0.05; (): p<0.01; (*): p<0.001.

FIG. 4: Schematic representation of kinases involved in CD90-downstream signaling with their corresponding chemical and genetic inhibitors was represented in (A). Schematic representation of dasatinib effects on GBM stem and non-stem cells described in this study was represented in (B).

EXAMPLE

Material & Methods

Reagents and antibodies—All reagents not specified below were purchased from Sigma-Aldrich (St Quentin Fallavier, France). Antibodies against human CD90, FAK, and phosphoFAK were obtained from BD Biosciences (Le Pont de Claix, France); anti-CD90 antibody used for immunohistochemistry from Novus Biologicals (Bio-Techne, Lille, France); anti-RhoA antibody from Santa Cruz Biotechnology (CliniSciences, Nanterre, France); anti-SRC and anti-phosphoSRC antibodies from Cell Signaling Technology (Saint Quentin Yvelines, France).

Tumor specimens and cell culture—GBM samples were obtained after informed consent from patients admitted to the neurosurgery department at Rennes University Hospital for surgical resection in accordance with the local ethic committee. Tumors used in this study were histologically diagnosed as grade IV astrocytoma according to the WHO criteria. For transcriptome analysis, we retrospectively recruited a local cohort of 77 GBM patients treated with radiotherapy and concurrent/adjuvant temozolomide in accordance with the standard of care. Tumor samples were snap-frozen immediately after resection. All samples presented at least 70% of tumor cells. The extent of surgery was evaluated with an enhanced magnetic resonance imaging (MRI) performed within 24 hours after the resection. Adherent (RADH) and neurospheres (RNS) (enriched in stem cells) GBM primary cell lines were obtained from GBM samples as described in Avril et al., 2010 (Avril, T., et al., Distinct effects of human glioblastoma immunoregulatory molecules programmed cell death ligand-1 (PDL-1) and indoleamine 2,3-dioxygenase (IDO) on tumour-specific T cell functions. J Neuroimmunol, 2010. 225(1-2): p. 22-33). RADH cells were grown in Dulbecco's Modification of Eagle's Medium (DMEM, Lonza, Verviers, Belgium) supplemented with 10% foetal bovine serum (FBS) (Lonza). RNS cells were grown in DMEM/Ham's:F12 (Lonza) supplemented with B27 and N2 additives (Invitrogen, Cergy Pontoise, France), EGF (20 ng/ml) and basic FGF (20 ng/ml) (Peprotech, Tebu-Bio). All GBM RNS and RADH cells were used between the 5th and 15th passages for the experiments. Human immortalized U251 and U87 GBM cell lines were cultured in DMEM 10% FBS.

Preparation of CD90 knocked-down U251 and CD90 expressing U87 GBM cell lines—U251 cells were transfected with pLKO.1-puro plasmids containing shRNA constructs targeting CD90 mRNA and targeting non-mammalian mRNA (Sigma-Aldrich) using the Lipofectamine 2000 reagent (Life Technologies, St Aubin, France) according to the manufactor's instructions. After one week of culture under the selective antibiotic puromycin used at 10 µg/ml, transfected U251 cells were amplified and then cloned in 96-well plates at 0.1 cell/well. CD90 knocked-down U251 cell lines were expanded and selected for their decreased expression of CD90. U87 cells were transfected with CD90 cDNA (GeneWiz, Sigma-Aldrich) cloned into the pLKO.1-puro plasmid with EcoRI and BamHI enzymes using the Lipofectamine 2000 reagent. CD90 expressing U87 cell lines were obtained as described above with U251 and were selected for their high expression of CD90.

Preparation of CD90 knocked-down RADH and RNS GBM primary cell lines—RADH and RNS cells were infected with lentiviral particles generated from HEK293T cells using Lenti-X packaging single shot system (Takara, Ozyme) and pLKO.1-puro plasmids containing shRNA constructs targeting CD90 mRNA and CTR targeting non-mammalian mRNA using according to the manufactor's instructions. After one week of culture under puromycin selection used at 10 µg/ml, RNS cells were amplified and selected for their down-regulation of CD90 expression.

Orthotopic mouse model—Eight-weeks old male Balb/c NOD-SCID mice (Janvier, Saint Berthevin, France) were housed in an animal care unit authorized by the French Ministries of Agriculture and Research (Biosit, Rennes, France—Agreement No. B35-238-40). Parental, transfected U87 cells (50,000 cells/mouse) and RNS cells (50,000 cells/implantation) were orthotopically implanted in immunocompromised mice as described in Drogat, B., et al., 2007 (Drogat, B., et al., IRE1 signaling is essential for ischemia-induced vascular endothelial growth factor-A expression and contributes to angiogenesis and tumor growth in vivo. Cancer Res, 2007. 67(14): p. 6700-7). Mice were daily clinically monitored and sacrificed 28 days after implantation. Mouse brains were collected, fixed in formaldehyde solution 4% and paraffin embedded for histological analysis after H&E staining. Tumor burden was compared in the different groups of mice and analyzed using ImageJ software. For dasatinib treatment, mice were fed daily with dasatinib (40 mg/kg, Selleckchem, Euromedex, Souffelweyersheim, France) one week after implantation and for 3 weeks.

Gene expression data analysis—For transcriptome analysis using a local GBM cohort, total RNA was isolated with the NucleoSpin RNAII Kit (Macherey-Nagel, Hoerdt, France). RNA integrity (RNA Integrity Number ≥8) was confirmed with an Agilent 2100 bioanalyzer (Agilent Technologies, Les Ulis, France). Gene expression profiling was carried out with the Agilent whole human genome 8x60K microarray kit (Agilent Technologies). Total RNA was extracted, labelled and hybridized according to the kit manufacturer's recommendations. Raw intensity data were log 2-transformed and normalized (intra-array and inter-array scaling) using GeneSpring software (Agilent Technologies). Student t-tests with a Welch approximation were used to compare expression values between conditions. Adjusted p values were calculated by controlling for the false discovery rate with the Benjamini & Hochberg procedure. Genes were considered significantly differentially expressed if the p value was below 0.05 and the absolute fold-change was greater than 2.

Western blotting—Cells were lysed in ice-cold lysis buffer (30 mM Tris-HCl, pH 7.5, 150 mM NaCl, 1.5% CHAPS). Proteins were resolved by SDS-polyacrylamide gel electrophoresis (12%, 10% and 7% polyacrylamide gels for FAK and RhoA, phosphotyrosine, SRC proteins respectively) and transferred to nitrocellulose membrane for blotting. The membranes were blocked with 3% bovine serum albumin in 0.1% Tween 20 in PBS and incubated with the diluted primary antibodies (1/1000). Antibody binding was detected with the appropriate horseradish peroxidase-conjugated secondary antibodies (1/7000) (anti-rabbit or anti-mouse) (Dako) and visualized with ECL (KPL, Eurobio, Courtaboeuf, France) according to the manufacturer's instructions. Kinase phosphorylation intensities were relative to total corresponding kinase signals using ImageJ.

Immunohistochemistry—Human GBM and mouse brain sections were deparaffinised with EZ prep solution (Ventana Medical Systems, Tucson, United-States of America) at 75° C. for 8 minutes. Antigen retrieval was performed using Tris based buffer solution CC1 at 95° C. for 48 minutes and endogen peroxidase was blocked. After rinsing, slides were incubated at 37° C. for 60 minutes with diluted (1/50) primary antibodies against CD90. Signal enhancement was performed using the DABMap kit (Ventana Medical Systems). Detection kit procedure was optimized on the discovery instrument (Ventana Medical Systems).

Flow cytometry—Cells were washed in PBS 2% FBS and incubated with saturating concentrations of human immunoglobulins and fluorescent-labelled primary antibodies for 30 minutes at 4° C. Cells were then washed with PBS 2% FBS and analyzed by flow cytometry using a FACSCanto II flow cytometer (BD Biosciences). The population of interest was gating according to its FSC/SSC criteria. In most of the experiments, the dead cell population was excluded using 7-amino-actinomycin D (7AAD) staining (BD Biosciences). Data were analyzed with the FACSDiva (BD Biosciences) or the FlowJo software (Tree Star Inc., Ashland, United States) and the results were expressed as specific fluorescence intensity given by the ratio of geometric mean of test/geometric mean of the isotype control.

Boyden chamber migration assay—Parental, controls and transfected U251 and U87 cell lines were washed in DMEM, placed in Boyden chambers ($10^5$ cells/chamber in DMEM) that were placed in DMEM 20% FBS and incubated at 37° C. for 24 hours. After 24 hours, Boyden chambers were washed in PBS and cells were fixed in PBS 0.5% paraformaldehyde. Non-migrated cells inside the chambers were removed and cells were then stained with Giemsa (RAL Diagnostics, Martillac, France). After washes in PBS, pictures of 5 different fields were taken. Migration was given by the mean of number of migrated cells observed per field. For inhibition with chemical drugs, cells were pre-incubated 15 minutes with 10 µM of SRC family kinases inhibitors PP2 (Sigma-Aldrich) and dasatinib; of ROCK inhibitor Y27632 (Selleckchem) and with 1 µM of FAK inhibitor Y15 (Sigma-Aldrich). Kinases inhibitors were kept during the time of migration assay. For inhibition with siRhoA, cells were transfected without (siØ), with siGL2 (control) and siRhoA 48 hours before the migration assay.

MRI analysis—Eighty-nine treatment-naive GBM patients (males: n=59; females: n=30; median age=59 years—from 14 to 89 years) from the Cancer Genome Atlas (TCGA) cohort were analyzed for CD90 expression from transcriptome data and corresponding pretreatment MR imaging data. The images were downloaded from the NCI's The Cancer Imaging Archive (TCIA) (http://cancerimagingarchive.net/). Preoperative qualitative and semi-quantitative imaging variables were provided by the Visually Accessible Rembrandt Images (VASARI) feature set. Details of the imaging variables and acquisition were published previously (Zinn, P. O., et al., Radiogenomic mapping of edema/cellular invasion MRI-phenotypes in glioblastoma multiforme. PLoS One, 2011. 6(10): p. e25451). Medians of the CD90 mRNA expression level between each VASARI feature were compared using the Mann-Whitney test. Kaplan-Meier analysis was used to estimate the survival difference between different imaging features.

Statistics—Values represent the mean±SD of n different experiments. Student t-test was applied using a two-tailed distribution of two conditions of unequal or equal variances on groups of data obtained in experiments. The significance level was $p<0.05$.

Results

CD90 is Expressed on Stem and Non-Stem GBM Cells.

Figures 1B, 1C:
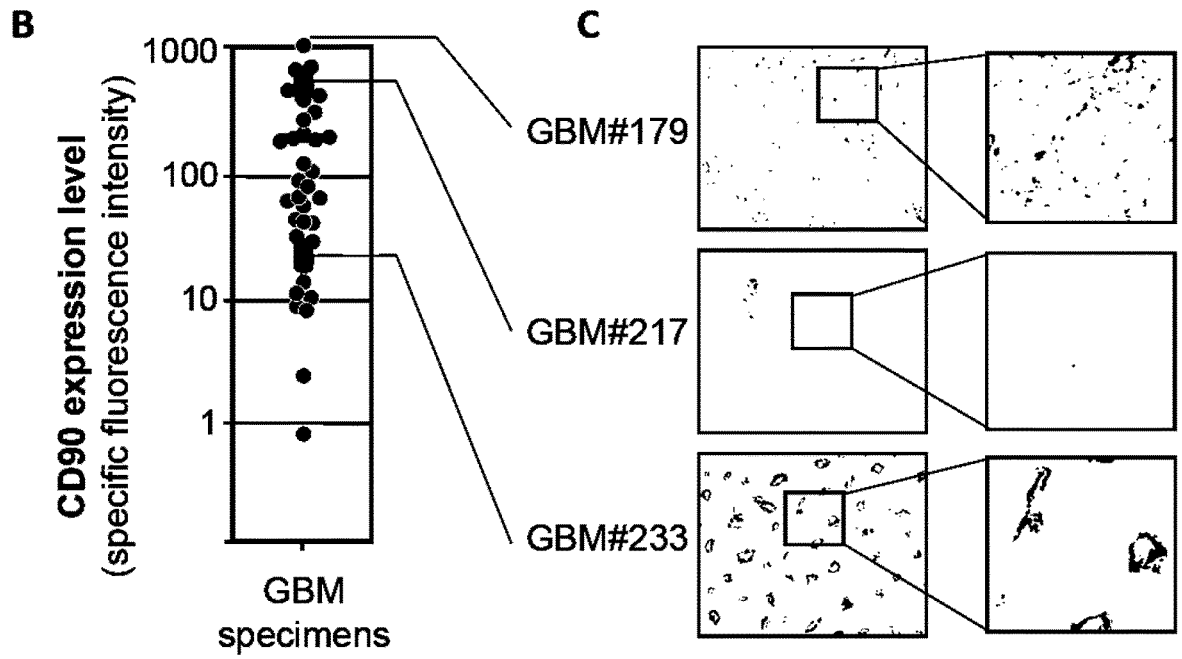

CD90 is expressed on human GSCs, GASCs and mesenchymal stem cell-like pericytes. However, we previously observed expression of CD90 on human adherent primary GBM cells, which do not display stem-like characteristics. To clarify this discrepancy, analysis of dissociated GBM samples (n=36) revealed that CD90 was expressed in most GBM specimens tested (34 out of 36) (FIGS. 1A and 1B) with various intensities (around 3 logs variation of specific fluorescence intensity) (FIG. 1B). CD90 expression was confirmed using immunohistochemistry on high (GBM #179) and intermediate (GBM #217) CD90 expressing specimens with a clear staining on most tumor cells and on blood vessels (FIG. 1C). A staining restricted to the vessels was only observed in the $CD90^{low}$ sample (GBM #233) (FIG. 1C). These results show that CD90 expression is not restricted to stem-like GBM cells but it is also expressed on more differentiated tumor cells.

CD90 is Associated with a Cell Adhesion/Migration Gene Signature and Invasive Tumors in Gbm Patients.

Figure 1D:
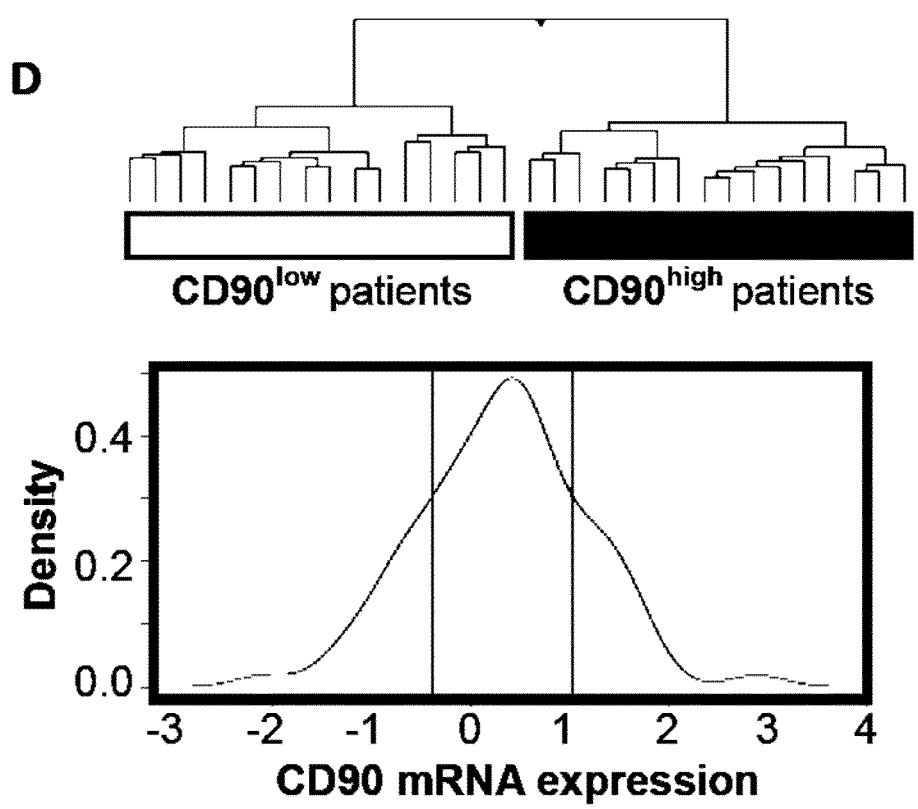
Figure 1E:
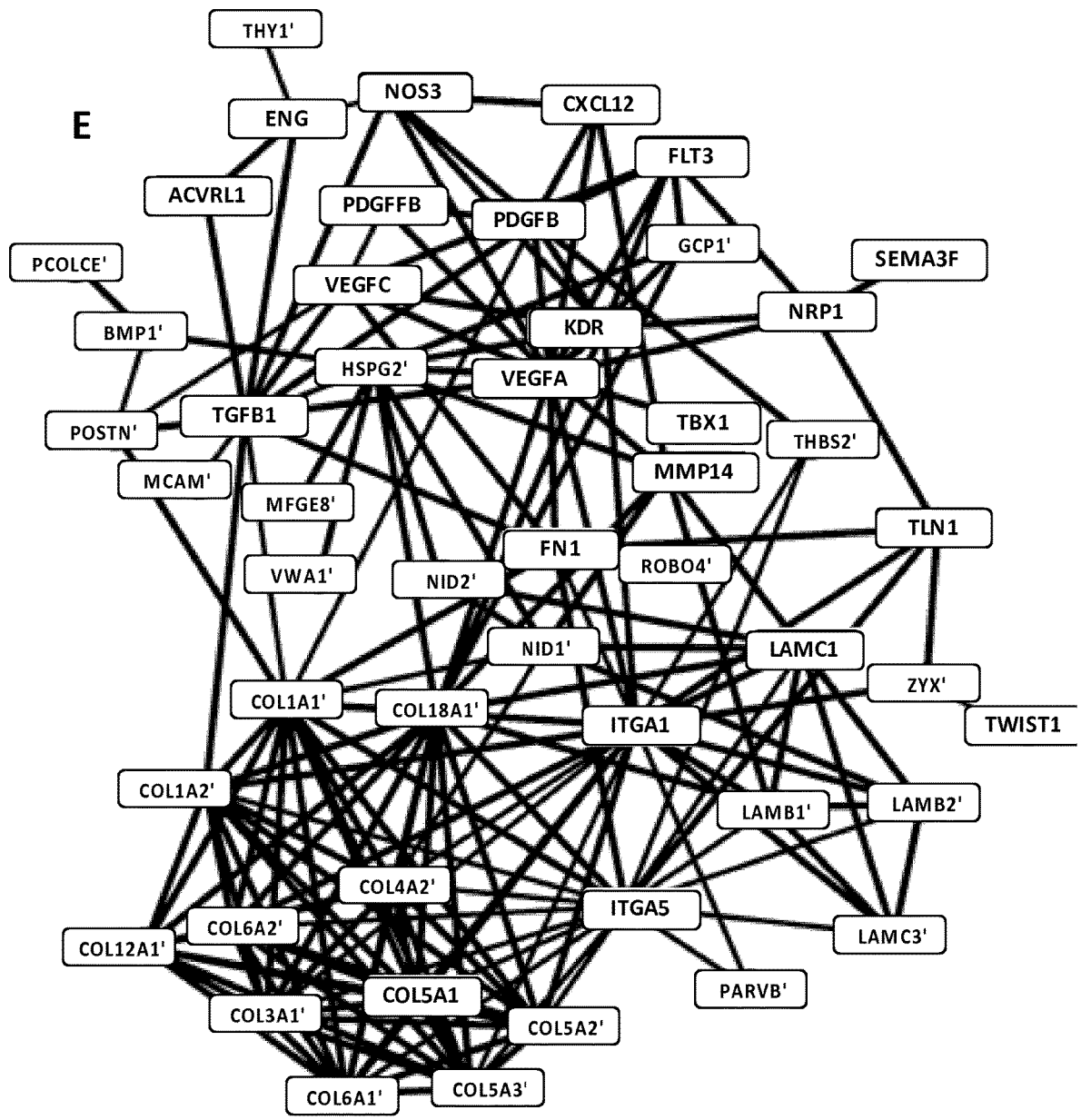
Figure 1F:
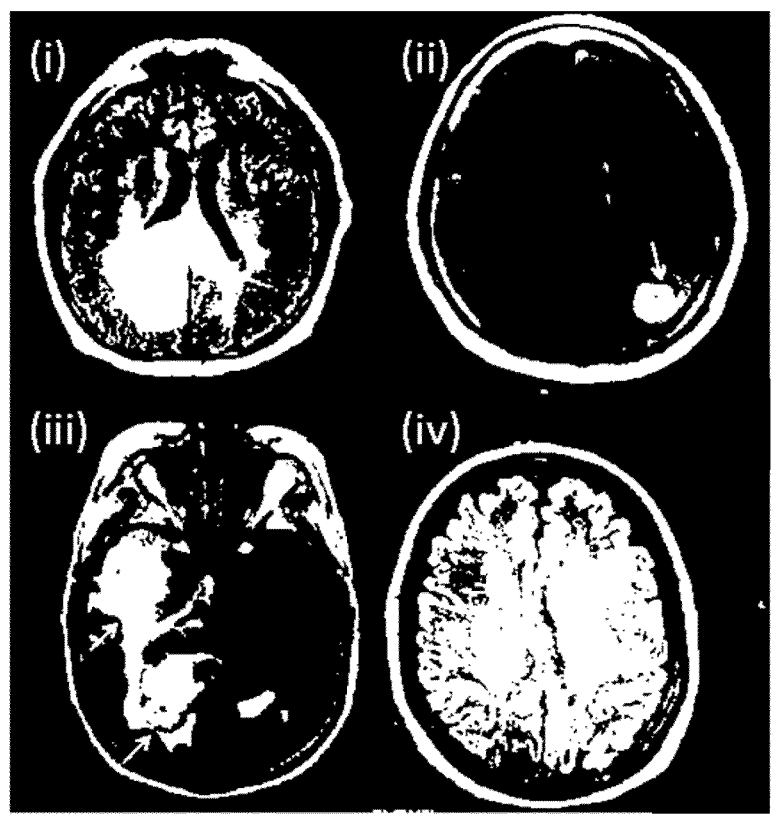
Figure 1G:
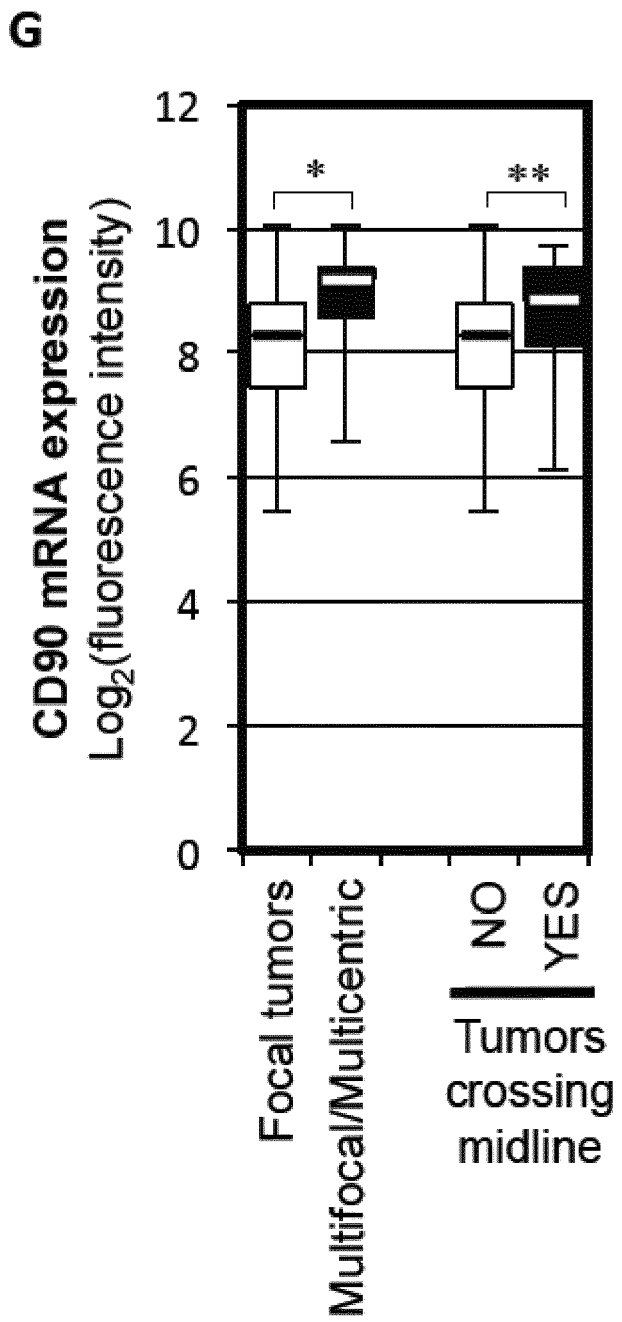

To better characterize the role of CD90 in GBM, gene expression profiling was performed on an in-house cohort of 77 GBM specimens (Table 1). Two group of 16 GBM patients were defined according to their CD90 expression level in the microarray data: $CD90^{low}$ patients exhibited a CD90 expression value lower than the $20^{th}$ percentile of the CD90 expression distribution, and $CD90^{high}$ patients had a CD90 expression value higher than the $80^{th}$ percentile of the CD90 expression distribution (FIG. 1D). Differential gene expression profiling revealed that $CD90^{high}$ tumors exhibited a cell adhesion/migration gene signature (Tables 2) that was also comprised within a highly connected network (FIG. 1E). These results show that CD90 expression is linked to a cell adhesion/migration gene signatures in GBM patients. Our data were then correlated to that obtained in patients' tumors from the TCGA cohort (Mazurowski, M. A., A. Desjardins, and J. M. Malof, Imaging descriptors improve the predictive power of survival models for glioblastoma patients. Neuro Oncol, 2013. 15(10): p. 1389-94). Indeed the Visually Accessible Rembrandt Images (VASARI) feature set was analyzed in 89 GBM patients from the TCGA cohort (Zinn, P. O., et al., Radiogenomic mapping of edema/cellular invasion MRI-phenotypes in glioblastoma multiforme. PLoS One, 2011. 6(10): p. e25451) and tested for associations with CD90 expression. Among all VASARI features, CD90 mRNA expression level was significantly different in non-enhancing tumor crossing midline versus those not crossing midline; and in multifocal/multicentric features versus focal tumors (FIGS. 1F and 1G). These data demonstrate that CD90 expression in tumor cells is associated with a more invasive tumor phenotype.

Modulation of CD90 Expression Affects Migration of GBM Cells In Vitro.

To study the role of CD90 in GBM cells, CD90 was silenced in $CD90^{high}$ U251 cells and CD90 expression was restored in CD90 negative U87 cells. Efficacy of silencing was verified using both flow cytometry (FIGS. 2A and 2C). Cell viability and proliferation were next analyzed over 5 days. Decreased CD90 expression in U251 or increased CD90 expression in U87 neither affected cell viability nor proliferation (data not shown) when compared to parental or mock-transfected cell lines. Cell migration was then evaluated using Boyden chamber-based migration assays (FIGS.

Figures 2E, 2F:
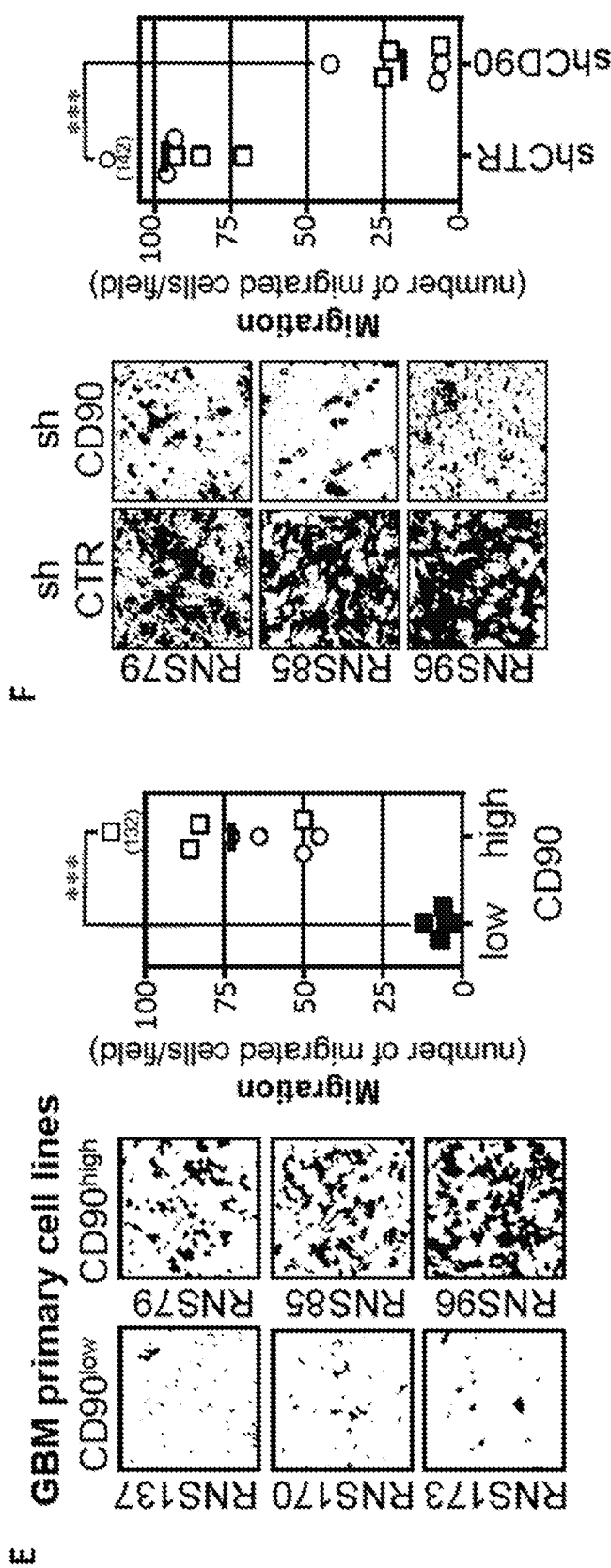

2B and 2D). In both cases, decreased expression of CD90 in U251 cells reduced migration and re-expression of CD90 in U87 increased migration. Similarly CD90$^{high}$ GBM primary lines exhibited stronger migration indexes than their CD90$^{low}$ counterparts (FIG. 2E). Furthermore shRNA-mediated silencing of CD90 in CD90$^{high}$ GBM primary lines dramatically reduced cell migration (FIG. 2F). Overall, these results show that CD90 expression does not impact on GBM cell viability or proliferation but is involved in their migration properties.

CD90 Expression Affects GBM Tumor Shape in Mice.

Parental and CD90 expressing U87 cells were tested for their tumorigenicity in an orthotopic xenograft mouse model. Most of the mice bearing parental U87 cells developed a clear encapsulated tumor mass 28 days post-injection that was evaluated by MRI and on brain sections stained with H&E staining (FIG. 2G; n=5 out of 7). Tumor formation was not detected in mice injected with U87 CD90 cells using MRI. However H&E staining revealed the presence of tumors with an irregular/invasive shape in mice injected with U87 CD90 cells (n=5 out of 7) whereas mice injected with parental U87 cells displayed one encapsulated tumor with regular edges (FIG. 2G). Moreover, CD90$^{low}$ and CD90$^{high}$ expressing RNS cells (n=2 and 4, respectively) were injected in an orthotopic xenograft mouse model. Clinical signs appeared between 76 and 140 days post-implantation, depending on the cell line but independent on CD90 expression (data not shown). Massive tumor infiltration within the brain parenchyma was observed with CD90$^{high}$ RNS cells contrasting with a more limited invasion observed with CD90$^{low}$ RNS cells (FIGS. 2H and 2I). These data are consistent with the results obtained in patients from the TCGA cohort and demonstrate that CD90 expression in tumor cells is associated with a more invasive tumor phenotype.

CD90 Signals Through SRC and FAK Molecules.

Figure 3A:
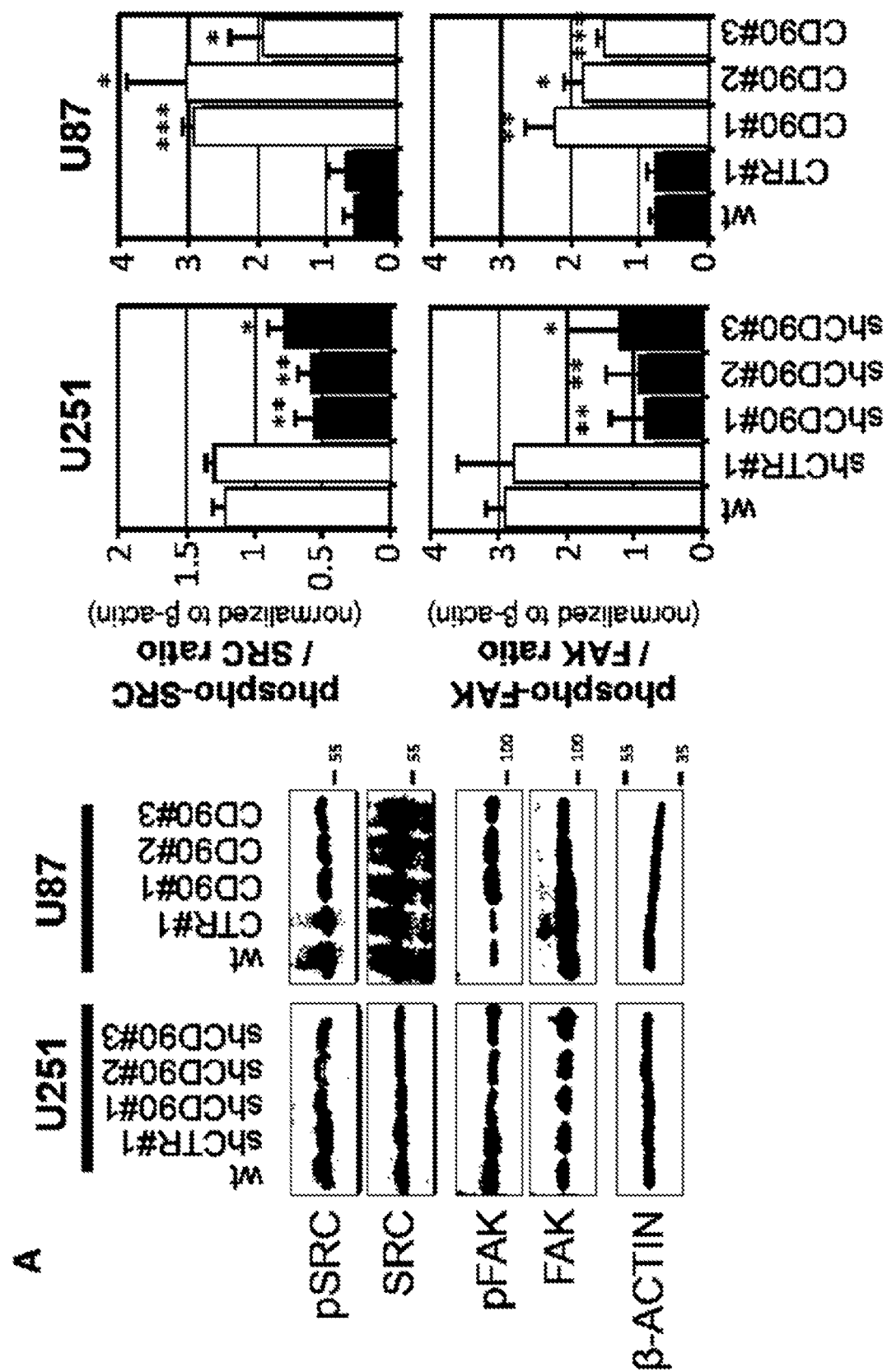
Figure 3B:
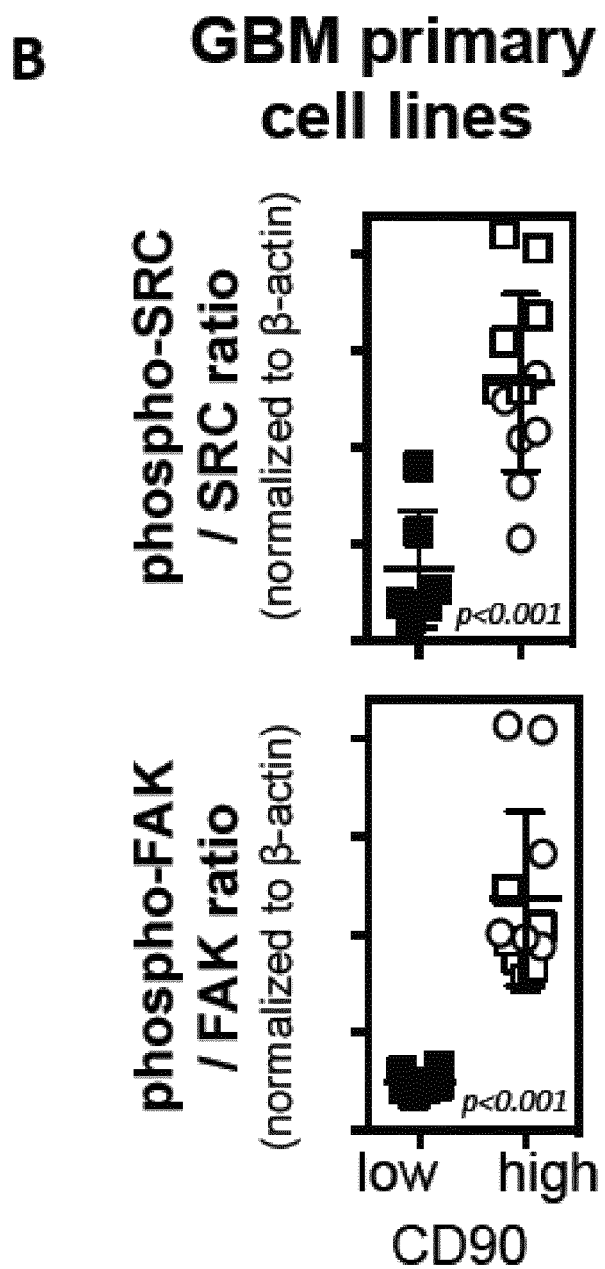

To investigate CD90-dependent signaling pathways, U251 shCD90 and U87 CD90 transfectants were analyzed for total phosphotyrosine containing proteins using Western blot in comparison to parental and U251 shCTR and U87 CTR cells, respectively (FIG. 3A). FAK and SRC kinases were previously described to interact with CD90 (Rege, T. A., et al., Thy-1, via its GPI anchor, modulates Src family kinase and focal adhesion kinase phosphorylation and subcellular localization, and fibroblast migration, in response to thrombospondin-1/hep I. Exp Cell Res, 2006. 312(19): p. 3752-67) and total SRC and FAK did not vary in CD90$^{high}$ and CD90$^{low}$ cell lines (FIG. 3A). However, increase in SRC and FAK tyrosine phosphorylation was observed in U87 CD90$^{high}$ cells (FIG. 3A). In contrast, a decrease in SRC and FAK phosphorylation was observed with U251 silenced for CD90 (FIG. 3A). Finally, increased phosphorylation of SRC and FAK was observed in CD90$^{high}$ GBM primary cells compared to CD90$^{low}$ primary cells (FIG. 3B). These data indicated that CD90 expression correlated with the activation of SRC and FAK signaling.

CD90-Dependent Migration is Mediated by SRC, FAK, RhoA and ROCK

Figures 3C, 3D:
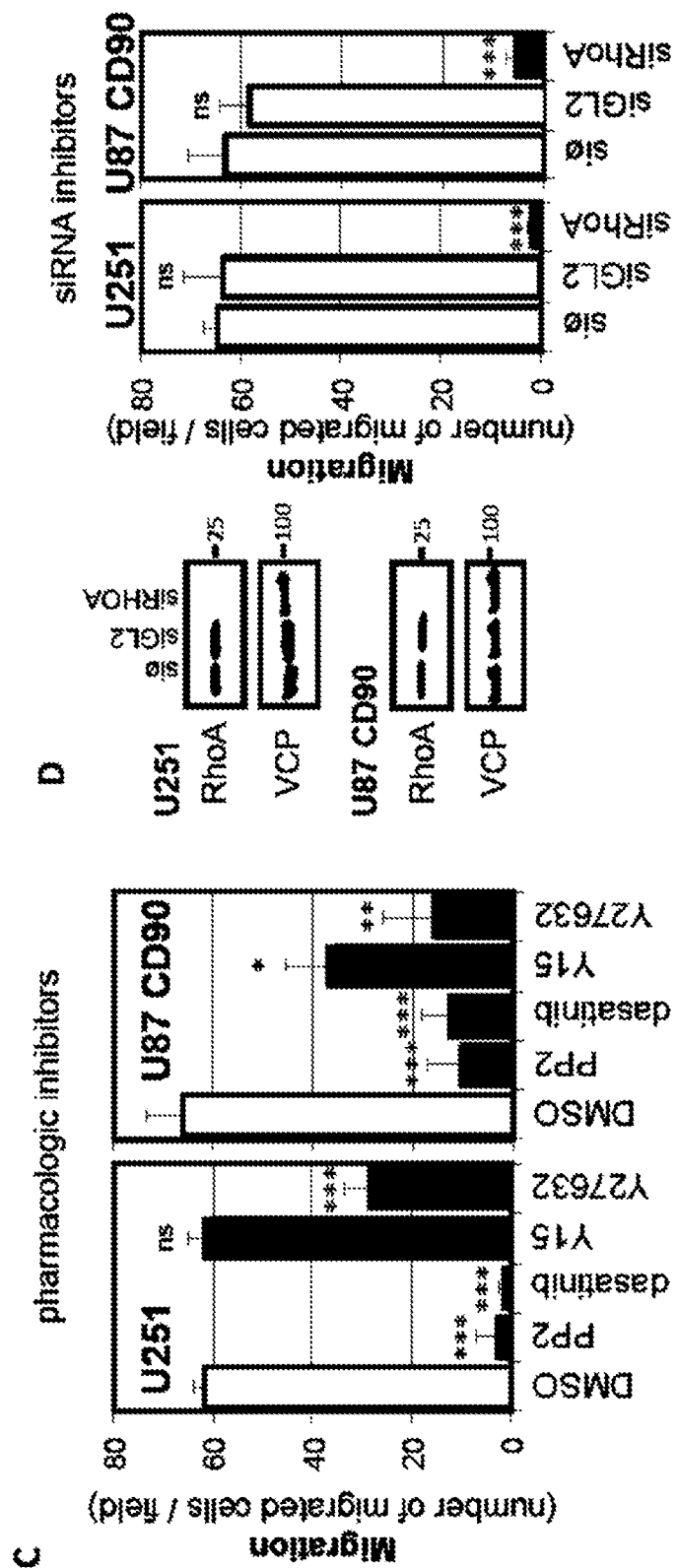
Figures 3E, 3F:
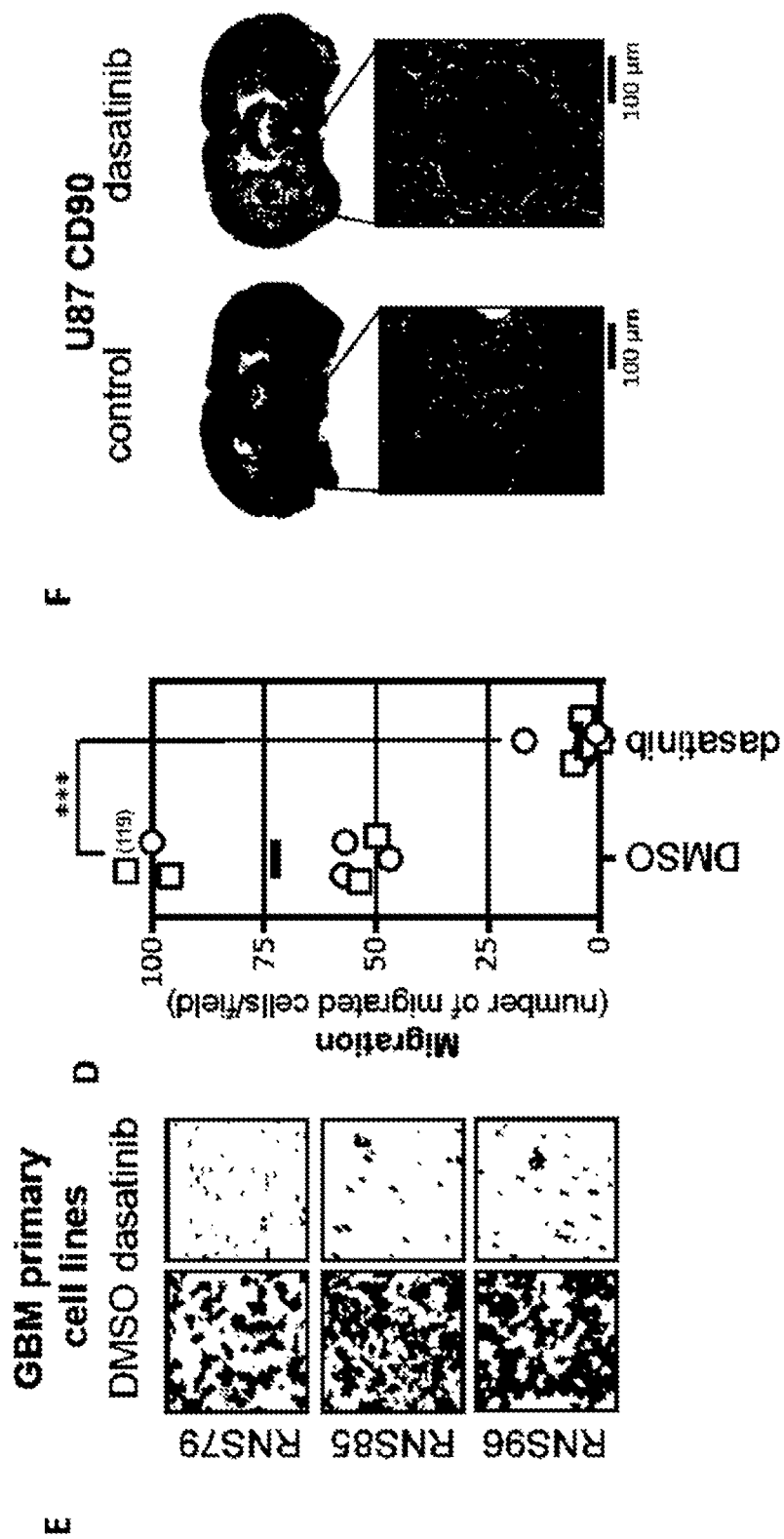
Figure 4A:
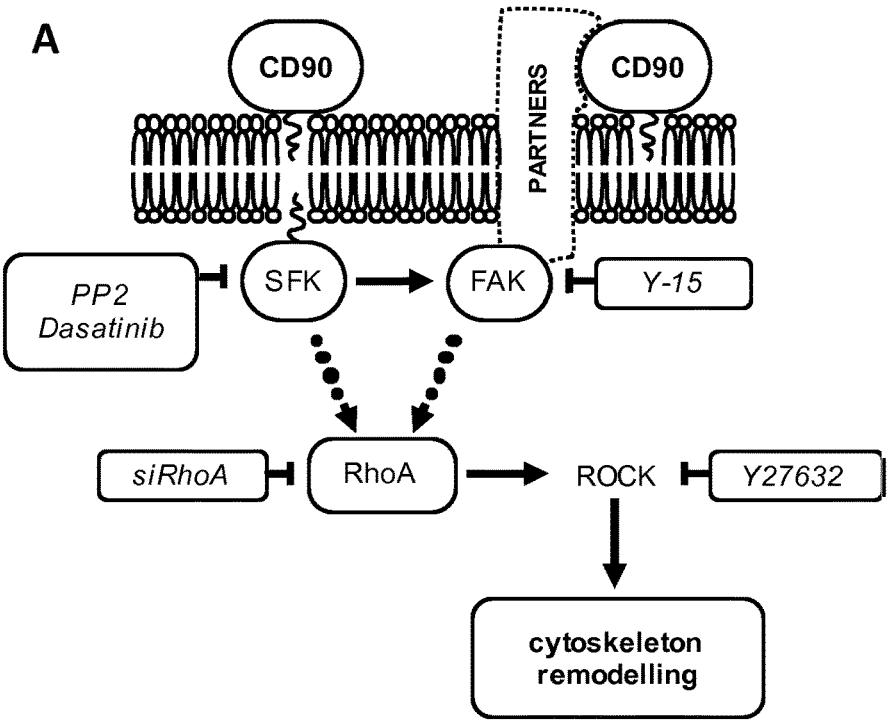

To confirm CD90 expression-dependent signaling toward cell migration in U251 and U87 cells, the chemical inhibitors PP2 and dasatinib, Y15 and Y27632 respectively for SRC family kinases, FAK and ROCK kinases were tested in Boyden chamber migration assays using parental U251 and U87 CD90 cells (FIG. 3C). These inhibitors had no effect on cell viability during the time of the assay and did not impact on the low migration property of U251 shCD90 #1 and parental U87 cells (data not shown). The SRC family kinases inhibitors PP2 and dasatinib dramatically reduced U251 and U87 CD90 cell migration. Migration inhibition was also observed upon treatment with the ROCK inhibitor Y27632 (53% and 76% reduction using U251 and U87 CD90 cells respectively) but to a lesser extent. In contrast, the FAK inhibitor Y15 had no or limited effect on the migration of U251 and U87 CD90 cells. Furthermore, siRNA-mediated RhoA silencing completely abrogated migration of U251 and U87 CD90 cells (FIG. 3D). Interestingly, dasatinib also dramatically reduced the migration of primary CD90$^{high}$ GBM lines (FIG. 3E). These results indicate that CD90-mediated migration mainly depends on the SRC family kinases, of ROCK and to a lesser extent of FAK (FIG. 4A).

Dasatinib Inhibits CD90-Mediated Migration of GBM Cells In Vivo.

To evaluate the CD90-dependent effects of dasatinib in vivo, U87 CD90 cells were used in an orthotopic xenograft mouse model. Mice were treated with dasatinib (40 mg/kg) for 20 days as soon as one week post-implantation. Mice were analyzed using MRI 28 days post-injection and were sacrificed. MRI of control non-treated U87 CD90 bearing mice did not revealed any detectable tumor formation whereas an irregular tumor mass was observed after H&E staining (FIG. 3F, n=6 out of 7). In contrast, clear encapsulated tumors with regular edges were observed using both MRI (n=3 out of 4) and H&E staining (FIG. 3F, n=4 out of 7) in mice injected with U87 CD90 and treated with dasatinib. Overall, the data demonstrates that dasatinib inhibits CD90 tumor migration/invasion properties in vivo.

Discussion

In this study, we show that CD90 is expressed on all GBM tumor cells (both stem and differentiated) and we demonstrate that CD90 expression controls tumor cell migration through SRC, RhoA and ROCK signaling. In addition, we show that CD90 expression regulates tumor invasive characteristics in mouse models and in human tumors. CD90 is also involved in cell-cell/matrix adhesion properties of GBM cells. Finally, we provide evidence that dasatinib dramatically reduces CD90-mediated invasiveness of U87 CD90 cells in vivo in an orthotopic xenograft mouse model and that CD90 expression impacts on dasatinib sensitivity in patient-derived cell lines. Collectively, this study unveils the importance of CD90 in GBM migration/invasion and could point toward CD90 expression as a predictor of dasatinib response in GBM patients.

CD90 has been previously described as a candidate marker for cancer stem cells from primary high-grade gliomas. More recently, CD90 positive cells were associated with blood vessels in human GBM tissues and characterized as immature mesenchymal stem cell-like pericytes. However, we observed CD90 expression on human adherent primary GBM cells and high CD90 mRNA amounts were reported on conventional and primary GBM cell lines as well as on tumor specimens. Using flow cytometry and immunohistochemistry approaches on GBM samples, we found that CD90 was highly expressed on endothelial cells within the tumor and on neurons present in the brain parenchyma as previously described (Bradley, J. E., G. Ramirez, and J. S. Hagood, Roles and regulation of Thy-1, a context-dependent modulator of cell phenotype. Biofactors, 2009. 35(3): p. 258-65) (Rege, T. A. and J. S. Hagood, Thy-1 as a regulator of cell-cell and cell-matrix interactions in axon regeneration, apoptosis, adhesion, migration, cancer, and fibrosis. FASEB J, 2006. 20(8): p. 1045-54). We also observed CD90 expression on GBM derived stem and more differentiated tumor cells using both cell lines and human tumor specimens.

One of the important features of GBM is the diffuse invasion of tumor cells throughout the surrounding brain parenchyma (Louis, D. N., et al., The 2007 WHO classification of tumours of the central nervous system. Acta Neuropathol, 2007. 114(2): p. 97-109), rendering a complete surgical resection impossible (Zhong, J., et al., Mesenchymal migration as a therapeutic target in glioblastoma. J Oncol, 2010. 2010: p. 430142). We showed that U87- or RNS-derived CD90$^{high}$ tumors displayed a more invasive phenotype in an orthotopic mouse model compared to their CD90$^{low}$ counterparts. This observation correlated with patients' data since CD90$^{high}$ tumors also presented VASARI invasive features. These CD90-dependent invasive features were then analyzed at both gene expression levels and signaling characteristics. Interestingly, CD90$^{high}$ GBM were characterized by an adhesion/migration gene signature and exhibited elevated expression of mesenchymal markers such as αSMA, COL1A1, COL1A2 and MMP-2 and -9. Over-expression of these specific genes could be related to the increased invasiveness observed in CD90$^{high}$ tumors. These properties of CD90$^{high}$ tumor cells could also involve the activation of specific signaling pathways downstream of CD90. Indeed, CD90 is known to interact with multiple signaling molecules such as p100, CD45, the SRC family kinases (SFK) LYN and FYN and small G proteins. CD90 also regulates actin and tubulin cytoskeleton reorganisation, focal disassembly, leading to modulation of cell migration. Herein, we demonstrate that CD90 controls GBM cell migration/invasion though SRC kinases, RhoA, ROCK and partially through FAK. The relevance of SRC signalling in CD90$^{high}$ GBM primary cell lines was confirmed by the identification of the SRC gene signature previously described by Bild et al. (Bild, A. H., et al., Oncogenic pathway signatures in human cancers as a guide to targeted therapies. Nature, 2006. 439(7074): p. 353-7) in those cells compared to CD90$^{low}$ counterparts. However, we cannot rule out that other SFK family members might also be involved. SRC and c-YES kinases have been recently involved in migration of glioma stem cells (Han, X., et al., The role of Src family kinases in growth and migration of glioma stem cells. Int J Oncol, 2014. 45(1): p. 302-10). However, we did not observe any c-YES activation in U251 and U87 lines modified for CD90 expression (data not shown). CD90 is also associated with the formation of actin stress fibers in GBM cells as a result of RhoA and ROCK activation. These signaling events drive cytoskeleton remodelling that are coordinated with changes in adhesion properties thereby promoting cell migration.

Figure 4B:
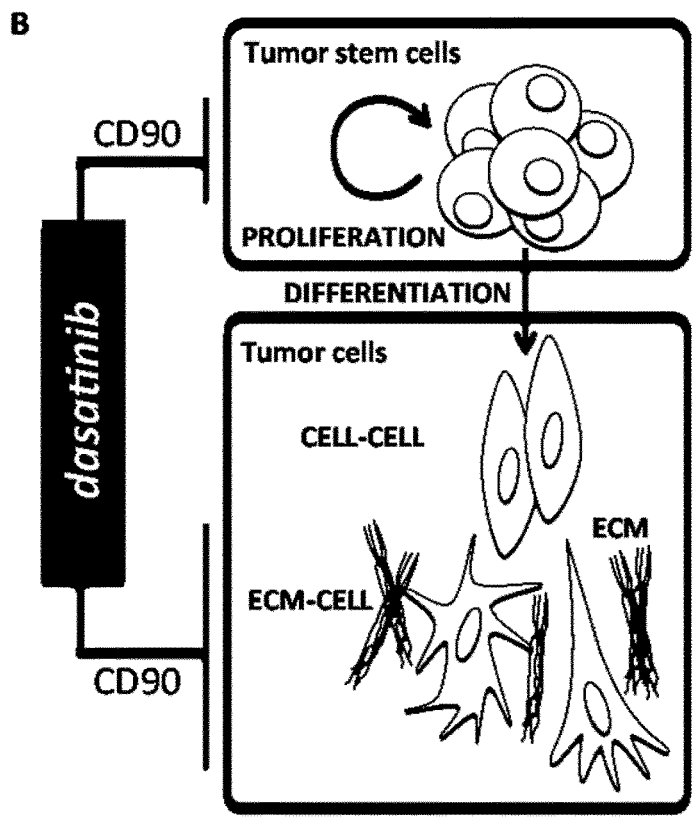

In the past few years, intensive research programs have identified new therapeutic agents that target glioma migration/invasion (Zhong, J., et al., Mesenchymal migration as a therapeutic target in glioblastoma. J Oncol, 2010. 2010: p. 430142.). For instance inhibition of metalloproteinases, blockade of integrins, targeting of cytoskeleton reorganisation and inhibition of signaling molecules such as FAK and SFK showed promising effects on GBM invasiveness in vitro and GBM progression in mouse models. Some of these molecules have also been used in recent GBM clinical trials. As such marimastat, an MMP inhibitor, showed encouraging effects on recurrent GBM patients (Groves, M. D., et al., Phase II trial of temozolomide plus the matrix metalloproteinase inhibitor, marimastat, in recurrent and progressive glioblastoma multiforme. J Clin Oncol, 2002. 20(5): p. 1383-8) but failed to improve patient survival in a phase III clinical trial (Levin, V. A., et al., Randomized, double-blind, placebo-controlled trial of marimastat in glioblastoma multiforme patients following surgery and irradiation. J Neurooncol, 2006. 78(3): p. 295-302). Cilengitide, a αvβ3 and αvβ5-integrins antagonist, combined with temozolomide showed limited effects on GBM patients (Stupp, R., et al., Cilengitide combined with standard treatment for patients with newly diagnosed glioblastoma with methylated MGMT promoter (CENTRIC EORTC 26071-22072 study): a multicentre, randomised, open-label, phase 3 trial. Lancet Oncol, 2014. 15(10): p. 1100-8). Dasatinib showed promising effect on inhibiting bevacizumab-induced glioma cell invasion at a preclinical phase, but failed to improve bevacizumab-treated recurrent GBM patients in a phase II trial (Lassman, A. B., et al., Phase 2 trial of dasatinib in target-selected patients with recurrent glioblastoma (RTOG 0627). Neuro Oncol, 2015. 17(7): p. 992-8). Interestingly, SFK family kinases including SRC, FYN, and c-YES are involved in glioma proliferation and motility in vitro. LYN and c-YES have opposite effects on survival in a glioma orthotopic xenograft model. However, we show in the present study that dasatinib affects viability of CD90$^{high}$ RNS cells and blocks CD90-mediated GBM migration in vivo. We propose a model that recapitulates our data underlining the rational to use dasatinib in CD90$^{high}$ GBM patients by targeting the GSC proliferation as well as GBM migration (FIG. 4B). Our results strongly emphasize the need of re-addressing dasatinib response in GBM patients following a CD90-based stratification.

In conclusion, our data point towards CD90 as a marker of tumor invasion and might also be considered as a GBM stratification tool for clinical trials testing new therapeutic agents that target SRC-dependent GBM migration/invasion. Our results might also open new directions for therapeutic approaches targeting CD90 and its downstream signaling to be applied to GBM patients.

TABLE 1

Patients demographic and clinical characteristics

| | | |
|---|---|---|
| Gender | male | n = 54 |
| | female | n = 23 |
| Age (years) | median [range] | 60 [36-75] |
| Karnofsky performance score (%) | median [range] | 90 [50-100] |
| | ≤70% | 12 |
| | >70% | 38 |
| | missing | 12 |
| Treatment (resection) | biopsy | n = 4 |
| | partial | n = 17 |
| | complete | n = 55 |
| | missing | n = 1 |
| MGMT status | methylated | n = 29 |
| | unmethylated | n = 48 |
| IDH1 status | wild-type | n = 20 |
| | mutated | n = 1 |
| | missing | n = 56 |
| Subtypes | classical | n = 17 |
| | mesenchymal | n = 28 |
| | neural | n = 14 |
| | proneural | n = 18 |
| Overall survival (months) | median [95% CI] | 17.5 [15.9-19.6] |
| Progression-free Survival (months) | median [95% CI] | 10.8 [9.6-13.9] |

TABLE 2

Top10 genes up-regulated in CD90$^{low}$ and CD90$^{high}$ GBM patients*

| GeneSymbol | Probe Name | Gene Name | Fold Change (CD90high/CD90low) | p |
|---|---|---|---|---|
| MMP9 | A_23_P40174 | Matrix metalloproteinase-9 | 8.69 | >0.0001 |
| COL1A1 | A_33_P3304668 | Collagen alpha-1(I) chain | 8.05 | >0.0001 |
| POSTN | A_33_P3511265 | Periostin | 6.83 | 0.0027 |
| NOS2 | A_23_P502464 | Nitric oxide synthase, inducible | 6.69 | 0.0011 |
| MXRA5 | A_23_P258136 | Matrix-remodeling-associated protein 5 | 6.33 | >0.0001 |
| PXDNL | A_23_P258310 | Peroxidasin-like protein | 6.22 | 0.0002 |
| SPON2 | A_23_P121533 | Spondin-2 | 6.21 | >0.0001 |
| BDKRB2 | A_23_P304897 | B2 bradykinin receptor | 5.66 | >0.0001 |
| CD248 | A_33_P3337485 | Endosialin | 5.50 | >0.0001 |
| COL1A2 | A_24_P277934 | Collagen alpha-2(I) chain | 5.34 | >0.0001 |
| HBD | A_24_P75190 | Hemoglobin subunit delta | -3.10 | 0.0017 |
| RGS1 | A_23_P97141 | Regulator of G-protein signaling 1 | -2.94 | 0.0003 |
| RNU2-2 | A_33_P3279708 | RNA, U2 small nuclear 2 | -2.85 | 0.0009 |
| SLC1A3 | A_21_P0000065 | Excitatory amino acid transporter 1 | -2.68 | 0.0004 |
| HBB | A_23_P203558 | Hemoglobin subunit beta | -2.68 | 0.0021 |
| SNHG5 | A_19_P00322944 | Small nucleolar RNA host gene 5 (non-protein coding) | -2.54 | 0.0011 |
| LYG1 | A_23_P165707 | Lysozyme g-like protein 1 | -2.53 | 0.0001 |
| CCDC7 | A_33_P3385842 | Coiled-coil domain-containing protein 7 | -2.35 | 0.0005 |
| SNORA71B | A_21_P0000294 | Small Nucleolar RNA, H/ACA Box 71B | -2.34 | 0.001 |
| SNORA16B | A_21_P0000494 | Small Nucleolar RNA, H/ACA Box 16B | -2.33 | 0.0001 |

*CD90$^{low}$ and CD90$^{high}$ tumors exhibit differential gene profiles as described in FIG. 4. Top10 up-regulated genes for CD90$^{low}$ (☐) and CD90$^{high}$ (■) groups are listed in this table.

REFERENCES

Throughout this application, various references describe the state of the art to which this invention pertains. The disclosures of these references are hereby incorporated by reference into the present disclosure.

The invention claimed is:

1. A method of treating glioblastoma with a drug selected from the group consisting of SRC inhibitor, FAK inhibitor and RhoA inhibitor in an eligible subject in need thereof comprising
   i) determining the expression level of CD90 in a sample comprising glioblastoma cells obtained from the subject,
   ii) comparing the expression level determined at step i) with a predetermined reference level,
   iii) identifying that the subject is eligible for treatment when the expression level determined at step i) is higher than the predetermined reference level, and
   iv) administering a therapeutically effective amount of the drug selected from the group consisting of SRC inhibitor, FAK inhibitor and RhoA inhibitor to the subject, wherein the therapeutically effective amount is sufficient to inhibit at least one property of the glioblastoma cells selected from the group consisting of cell adhesion, migration and invasion.

2. The method of claim 1 wherein the SRC inhibitor is dasatinib.

3. The method of claim 1 wherein the sample comprising glioblastoma cells further comprises differentiated glioblastoma tumor cells.

4. A method for treating glioblastoma multiforme (GBM) with dasatinib in an eligible subject in need thereof, comprising
   i) determining the expression level of CD90 in a sample comprising differentiated glioblastoma cells obtained from the subject,
   ii) comparing the expression level determined at step i) with a predetermined reference level,
   iii) identifying that the subject is eligible for treatment when the expression level determined at step i) is higher than the predetermined reference level, and
   iv) administering a therapeutically effective amount of the dasatinib to the subject, wherein the therapeutically effective amount is sufficient to inhibit at least one property of the differentiated glioblastoma cells selected from the group consisting of cell adhesion, migration and invasion.

5. The method of claim 4, wherein dasatinib is administered as the sole agent for treating GBM.

* * * * *